(12) United States Patent
Hammer et al.

(10) Patent No.: US 8,201,943 B2
(45) Date of Patent: Jun. 19, 2012

(54) ADAPTIVE OPTICS LINE SCANNING OPHTHALMOSCOPE

(75) Inventors: Daniel X. Hammer, Bedford, NH (US); R. Daniel Ferguson, Melrose, MA (US); Mircea Mujat, Acton, MA (US); Nicusor V. Iftimia, Chelmsford, MA (US)

(73) Assignee: Physical Sciences, Inc., Andover, MA (US)

( * ) Notice: Subject to any disclaimer, the term of this patent is extended or adjusted under 35 U.S.C. 154(b) by 0 days.

(21) Appl. No.: 12/688,217

(22) Filed: Jan. 15, 2010

(65) Prior Publication Data
US 2010/0195048 A1    Aug. 5, 2010

Related U.S. Application Data

(60) Provisional application No. 61/144,951, filed on Jan. 15, 2009.

(51) Int. Cl.
*A61B 3/14* (2006.01)
*A61B 3/00* (2006.01)
*A61B 3/10* (2006.01)

(52) U.S. Cl. ......... 351/206; 351/200; 351/210; 351/221

(58) Field of Classification Search ............... 351/200, 351/205–206, 210–212, 221
See application file for complete search history.

(56) References Cited

U.S. PATENT DOCUMENTS

| | | | |
|---|---|---|---|
| 4,264,152 A | 4/1981 | Crane | |
| 4,443,075 A | 4/1984 | Crane | |
| 4,561,436 A | 12/1985 | Munnerlyn | |
| 4,569,354 A | 2/1986 | Shapiro et al. | |
| 4,579,430 A * | 4/1986 | Bille | 351/206 |
| 4,764,005 A | 8/1988 | Webb et al. | |
| 4,765,730 A | 8/1988 | Webb | |
| 4,768,873 A | 9/1988 | Webb | |
| 4,768,874 A | 9/1988 | Webb et al. | |
| 4,781,453 A | 11/1988 | Kobayashi | |
| 4,856,891 A | 8/1989 | Pflibsen et al. | |
| 4,881,808 A | 11/1989 | Bille et al. | |
| 4,883,061 A | 11/1989 | Zeimer | |
| 4,886,351 A | 12/1989 | Sabban et al. | |
| 4,924,507 A | 5/1990 | Chao et al. | |

(Continued)

FOREIGN PATENT DOCUMENTS

EP          0 307 185          3/1989

(Continued)

OTHER PUBLICATIONS

Sakaguchi et al., "Amsler Grid Examination and Optical Coherence Tomography of a Macular Hole Caused by Accidental Nd: YAG Lasser Injury," *American Journal of Ophthalmology*, vol. 130, No. 3 (2000) pp. 355-356 (2 pgs.).

(Continued)

*Primary Examiner* — Dawayne A Pinkney
(74) *Attorney, Agent, or Firm* — Proskauer Rose LLP

(57) ABSTRACT

A first optical module scans a portion of an eye with a line of light, descans reflected light from the scanned portion of the eye and confocally provides output light in a line focus configuration. A detection device detects the output light and images the portion of the eye. A second optical module detects an optical distortion and corrects the optical distortion in the line of light scanned on the portion of the eye.

24 Claims, 19 Drawing Sheets

U.S. PATENT DOCUMENTS

| | | | |
|---|---|---|---|
| 4,931,053 | A | 6/1990 | L'Esperance, Jr. |
| 4,964,717 | A | 10/1990 | Koester |
| 5,029,220 | A | 7/1991 | Juday |
| 5,094,523 | A | 3/1992 | Reznichenko et al. |
| 5,098,426 | A | 3/1992 | Sklar et al. |
| 5,106,184 | A | 4/1992 | Milbocker |
| 5,122,135 | A | 6/1992 | Dürr et al. |
| 5,129,400 | A | 7/1992 | Makino et al. |
| 5,243,368 | A | 9/1993 | Ito et al. |
| 5,252,999 | A | 10/1993 | Sukigara et al. |
| 5,309,187 | A | 5/1994 | Crossman et al. |
| 5,347,329 | A | 9/1994 | Ota |
| 5,353,073 | A | 10/1994 | Kobayashi |
| 5,360,010 | A | 11/1994 | Applegate et al. |
| 5,360,424 | A | 11/1994 | Klopotek |
| 5,425,729 | A | 6/1995 | Ishida et al. |
| 5,430,509 | A | 7/1995 | Kobayashi |
| 5,437,274 | A | 8/1995 | Khoobehi et al. |
| 5,480,396 | A | 1/1996 | Simon et al. |
| 5,526,189 | A | 6/1996 | Heacock |
| 5,673,097 | A | 9/1997 | Heacock |
| 5,726,443 | A | 3/1998 | Immega et al. |
| 5,767,941 | A | 6/1998 | Ferguson |
| 5,777,719 | A | 7/1998 | Williams et al. |
| 5,778,016 | A | 7/1998 | Sucha et al. |
| 5,784,148 | A | 7/1998 | Heacock |
| 5,861,938 | A | 1/1999 | Heacock |
| 5,943,115 | A | 8/1999 | Ferguson |
| 5,949,520 | A | 9/1999 | Heacock |
| 5,976,502 | A | 11/1999 | Khoobehi et al. |
| 6,027,216 | A | 2/2000 | Guyton et al. |
| 6,099,127 | A | 8/2000 | Manivannan et al. |
| 6,186,628 | B1 | 2/2001 | Van de Velde |
| 6,195,202 | B1 | 2/2001 | Kusunose |
| 6,199,986 | B1 | 3/2001 | Williams et al. |
| 6,267,477 | B1 | 7/2001 | Karpol et al. |
| 6,275,718 | B1 | 8/2001 | Lempert |
| 6,299,311 | B1 | 10/2001 | Williams et al. |
| 6,305,804 | B1 | 10/2001 | Rice et al. |
| 6,331,059 | B1 | 12/2001 | Kudryashov et al. |
| 6,379,006 | B1 | 4/2002 | Eikelboom et al. |
| 6,471,691 | B1 | 10/2002 | Kobayashi et al. |
| 6,582,079 | B2 | 6/2003 | Levine |
| 6,758,564 | B2 | 7/2004 | Ferguson |
| 6,890,076 | B2 | 5/2005 | Roorda |
| 7,113,817 | B1 | 9/2006 | Winchester et al. |
| 7,118,216 | B2 | 10/2006 | Roorda |
| 7,284,862 | B1 | 10/2007 | Lai et al. |
| 7,452,080 | B2 | 11/2008 | Witberger et al. |
| 2003/0053026 | A1 | 3/2003 | Roorda |
| 2003/0231285 | A1 | 12/2003 | Ferguson |
| 2005/0012899 | A1 | 1/2005 | Ferguson |
| 2005/0146784 | A1 | 7/2005 | Vogt |
| 2005/0254008 | A1 | 11/2005 | Ferguson et al. |
| 2007/0252951 | A1* | 11/2007 | Hammer et al. ............. 351/221 |
| 2008/0088852 | A1 | 4/2008 | Rogers et al. |
| 2009/0275929 | A1* | 11/2009 | Zickler ............................ 606/5 |

FOREIGN PATENT DOCUMENTS

| | | |
|---|---|---|
| EP | 0 770 370 | 5/1997 |
| JP | 11-253403 | 9/1999 |
| WO | WO 90/09141 | 8/1990 |
| WO | WO 93/08877 | 5/1993 |
| WO | WO 95/28989 | 11/1995 |
| WO | WO 97/40405 | 10/1997 |
| WO | WO 03/105678 | 12/2003 |
| WO | WO 03/105679 | 12/2003 |
| WO | WO 2007/127291 A2 | 11/2007 |
| WO | 2009/095473 | 8/2009 |

OTHER PUBLICATIONS

Sasahara et al., "Optical Coherence Tomographic Observations Before and After Macular Hole Formation Secondary to Laser Injury," *American Journal of Ophthalmology*, vol. 136, No. 6 (2003) pp. 1167-1170. (4 pgs.).

Thibos et al., "Standards for Reporting the Optical Aberrations of Eyes," *Journal of Refractive Surgery*, vol. 18 (2002) pp. S652-S660. (9 pgs.).

Vogel et al., "Retinal Motion Estimation in Adaptive Optics Scanning Laser Ophthalmoscopy," *Optics Express*, vol. 14, No. 2 (2006) pp. 487-497. (11 pgs.).

Webb, et al., "Confocal Scanning Laser Ophthalmoscope," *Applied Optics*, vol. 26, No. 8 (1987) pp. 1492-1499. (8 pgs.).

White et al., "In Vivo Dynamic Human Retinal Blood Flow Imaging Using Ultra-High-Speed Spectral Domain Optical Doppler Tomography," *Optics Express*, vol. 11, No. 25 (2003) pp. 3490-3497. (8 pgs.).

Wojtkowski et al., "In Vivo Human Retinal Imaging by Fourier Domain Optical Coherence Tomography," *Journal of Biomedical Optics*, vol. 7, No. 3 (2002) pp. 457-463. (7 pgs.).

Wojtkowski et al., "Real-Time in Vivo Imaging by High-Speed Spectral Optical Coherence Tomography," *Optics Letters*, vol. 28, No. 19 (2003) pp. 1745-1747. (3 pgs).

Yun et al., "High-Speed Optical Frequency-Domain Imaging," *Optics Express*, vol. 11, No. 22 (2003) pp. 2953-2963. (9 pgs.).

Yun et al., "High-Speed Spectral-Domain Optical Coherence Tomography at 1.3 μm Wavelength," *Optics Express*, vol. 11, No. 26 (2003) pp. 3598-3604. (7 pgs.).

Bai Xue et al. "Photoreceptor Counting and Montaging of En-Face Retinal Images from an Adaptive Optics Fundus Camera" Journal of Optical Society of America A (Optics, Image Science and Vision) Opt. Soc. America USA LNKD-DOI:10.1364/JOSAA.24.001364, vol. 24, No. 5, May 2007, pp. 1364-1372, XP002576750 ISSN: 0740-3232 the whole document.

International Search Report for International Application No. PCT/US2010/021152, Date of Mailing Apr. 22, 2010 (4 pages total).

America National Standards Institute, Inc. "American National Standard for Safe Use of Lasers" *Laser Institute of America*, (2000). (185 pgs.).

Alt et al., "Selective Targeting ofthe Retinal Pigment Epithelium Using an Acousto-Optic Laser Scanner," *Journal of Biomedical Optics*, vol. 10(6) (2005) pp. 064014-1-064014-11. (11 pgs.).

Bigelow et al., "Compact Multimodal Adaptive-Optics Spectral-Domain Optical Coherence Tomography Instrument for Retinal Imaging," *Journal of the Optical Society of America A*, vol. 24, No. 5 (May 2007) pp. 1327-1336. (10 pgs.).

Cense et al., "In Vivo Depth-Resolved Birefringence Measurements of the Human Retinal Nerve Fiber Layer by Polarization-Sensitive Optical Coherence Tomography," *Optics Letters*, vol. 27, No. 18 (2002) pp. 1610-1612. (3 pgs.).

Curcio et al., "Packing Geometry of Human Cone Photoreceptors: Variation With Eccentricity and Evidence for Local Anisotropy," *Visual Neuroscience*, vol. 9 (1992) pp. 169-180. (12 pgs.).

de Boer et al., "Improved Signal-to Noise Ratio in Spectral-Domain Compared with Time-Domain Optical Coherence Tomography," *Optics Letters*, vol. 28, No. 21 (2003) pp. 2067-2069. (3 pgs.).

Department of Defense Handbook, "Laser Safety on Ranges and in Other Outdoor Areas," MIL-HDBK-828A, Appendix A: "Summary of Laser Safety Information for Fire Control Laser Systems." (136 pgs.).

Dreher et al., "Active Optical Depth Resolution Improvement of the Laser Tomographic Scanner," *Applied Optics*, vol. 28, No. 4 (1989) pp. 804-808. (5 pgs.).

Drexler W et al., "Enhanced Visualization of Macular Pathology With the Use of Ultrahigh-Resolution Optical Coherence Tomography," *Archives of Ophthalmology*, vol. 121 (2003) pp. 695-706. (12 pgs.).

Duncan J., et al., "High-Resolution Imaging with Adaptive Optics in Patients with Inherited Retinal Degeneration," Investigative Ophthalmology & Visual Science, vol. 48, No. 7, Jul. 2007, pp. 3283-3291.

Fercher et al., "Measurement of Intraocular Distances by Backscattering Spectral Interferometry," *Optics Communications*, vol. 117 (1995) pp. 43-48. (6 pgs.).

Fercher et al., "Optical Coherence Tomography—Principles and Applications," *Institute of Physics Publishing Reports on Progress in Physics*, vol. 66 (2003) pp. 239-303. (65 pgs.)

Ferguson et al., "A Line-Scanning Laser Ophthalmoscope (LSLO)," *Investigative Ophthalmology & Visual Science*, (2003). (2 pgs.).

Ferguson et al., "Tracking Optical Coherence Tomography," *Optics Letters*, vol. 29, No. 18 (2004) pp. 2139-2141. (3 pgs.).

Ferguson et al., "Wide-Field Express Retinal Hemodynamic Imaging With the Tracking Scanning Laser Ophthalmoscope," *Optics Express*, vol. 12, No. 21 (2004) pp. 5198-5208. (11 pgs.).

Ferguson, et al "Tracking Adaptive Optics Scanning Laser Ophthalmoscope," *Proceedings of SPIE*, vol. 6138 (2006) pp. 613810-1-613810-9. (9 pgs.).

Gray D.C., et al, "In vivo Fluorescence Imaging of Primate Retinal Ganglion Cells and Retinal Pigment Epithelial Cell," Tumbar, R., et al., vol. 14, Nov. 16, Aug. 7, 2006, pp. 7144-7158.

Hammer D. X., et al., "Foveal Fine Structure in Retinopathy of Prematurity: An Adaptive Optics Fourier Domain Optical Coherence Tomography Study," *Investigative Ophthalmology & Visual Science*, vol. 49, No. 5, May 2008, pp. 2061-2070.

Hammer et al, "Precision Targeting With a Tracking Adaptive Optics Scanning Laser Ophthalmoscope," *Presented at SPIE BIOS 2006 Advanced Biomedical and Clinical and Diagnostic Systems IV* (San Jose, CA), (Jan. 21-26, 2006), [online], [retrieved on Jul. 31, 2007]. Retrieved from the Internet <URL: http://www.psicorp.com/publications/PDF/sr-1256.pdf> (11 pgs.).

Hammer et al., "Active Retinal Tracker for Clinical Optical Coherence Tomography Systems," *Journal of Biomedical Optics*, in press. vol. 10(2) (2005) pp. 024038-1-024038-11. (11 pgs.).

Hammer et al., "Adaptive Optics Scanning Laser Ophthalmoscope for Stabilized Retinal Imaging," *Optics Express*, vol. 14, No. 8 (2006) pp. 3354-3367. (13 pgs.).

Hammer et al., "Advanced Scanning Methods With Tracking Optical Coherence Tomography," *Optics Express*, vol. 13, No. 20 (2005) pp. 7937-7947. (11 pgs.).

Hammer et al., "Compact Scanning Laser Ophthalmoscope With High-Speed Retinal Tracker," *Applied Optics*, vol. 42, No. 22 (2003) pp. 4621-4632. (12 pgs.).

Hammer et al., "Hand-Held Digital Line-Scanning Laser Ophthalmoscope (LSLO)," *Proceedings of SPIE*, vol. 5314 (2004) pp. 161-169. (9 pgs.).

Hammer et al., "High Resolution Retinal Imaging With a Compact Adaptive Optics Spectral Domain Optical Coherence Tomography System," *Proceedings of SPIE*, vol. 6426 (2007) pp. 64261Q-1-64261Q-10. (10 pgs.).

Hammer et al., "Image Stabilization for Scanning Laser Ophthalmoscopy," *Optics Express*, vol. 10, No. 26 (2002) pp. 1542-1549. (8 pgs.).

Hammer et al., "Line-Scanning Laser Ophthalmoscope," *Journal of Biomedical Optics*, vol. 11(4) (2006) pp. 041126-1-041126-10. (10 pgs.).

Hammer et al., "Tracking Scanning Laser Ophthalmoscope (TSLO)," *Proceedings of SPIE*, vol. 4951 (2003) pp. 208-217. (10 pgs.).

Hammer, et al. "Hybrid LSLO/SDOCT retinal imager," [online], [retrieved on Jul. 31, 2007]. Retrieved from the Internet <URL:http://www.psicorp.com/publications/PDF/sr-1287.pdf> (9 pgs.).

Hammer, et al., "Technological Advances Improve Retinal Diagnostics," *Biophotonics International*, vol. 10, No. 9 (2003) p. 20. (2 pgs.).

Hausler et al., "'Coherence Radar' and 'Spectral Radar'—New Tools for Dermatological Diagnosis," *Journal of Biomedical Optics*, vol. 3, No. I (1998) pp. 21-31. (11 pgs.).

Heacock et al., "Imaging of the Choroid With the Scanning Slit Laser Ophthalmoscope (SSLO)," *The Society for Photo-Optical Instrumentation Engineers (SPIE)*, vol. 3591 (1999) pp. 456-464. (9 pgs.).

Huang et al., "Optical Coherence Tomography," *Science*, vol. 254 (1991) pp. 1178-1181. (4 pgs.).

Iftimia, et al. "Hybrid Retinal Imager Using Line-Scanning Laser Ophthalmoscopy and Spectral Domain Optical Coherence Tomography," *Optics Express*, vol. 14, No. 26 (2006) pp. 12909-12914. (12 pgs.).

Ishikawa et al., "Retinal Nerve Fiber Layer Assessment Using Optical Coherence Tomography With Active Optic Nerve Head Tracking," *Investigative Ophthalmology & Visual Science*, vol. 47, No. 3 (2006) pp. 964-967. (4 pgs.).

Johnson et al., "Laser Eye Injuries Among US Military Personnel," *Proceedings of SPIE*, vol. 4953 (2003) pp. 51-60. (10 pgs.).

Kobayashi et al., "Confocal Scanning Laser Ophthalmoscope With a Slit Aperture," *Measurement Science and Technology*, vol. 2 (1991) pp. 287-292. (6 pgs.)

Leitgeb et al., "Performance of Fourier Domain vs. Time Domain Optical Coherence Tomography," *Optics Express*, vol. 11, No. 8 (2003) pp. 889-894 (6 pgs.).

Liang et al., "Supernormal Vision and High-Resolution Retinal Imaging Through Adaptive Optics," *Journal of the Optical Society of America A*, vol. 14, No. 11 (1997) pp. 2884-2892. (9 pgs.).

Martin, J. A., et al., "Direct and Noninvasive Assessment of Parafoveal Capillary Leukocyte Velocity," American Academy of Ophthalmology, vol. 112, No. 12, Dec. 2005.

Nassif et al., "In Vivo High-Resolution Video-Rate Spectral-Domain Optical Coherence Tomography of the Human Retina and Optic Nerve," *Optics Express*, vol. 12, No. 3 (2004) pp. 367-376. (10 pgs.).

Park et al., "Real-Time Multi-Functional Optical Coherence Tomography," *Optics Express*, vol. 11, No. 7 (2003) pp. 782-793. (12 pgs.).

Patton N. et al., "Retinal Image Analysis: Concepts, Applications and Potential" Progress in Retinal and Eye Research, Oxford, GB LNKD- DOI:10.1016/J.Preteyeres,2005.07.001, vol. 25, No. 1, Jan. 1, 2006, pp. 99-127, XP025245981, ISSN: 1350-9462 [retrieved on Jan. 1, 2006] Chapter 1, Chapter 2.3.

Podoleanu A. GH et al., "Combinations of Techniques in Imaging the Retina with High Resolution," Progress in Retinal and Eye Research, Oxford, GB LNKD- DOI:10.1016/J.Preteyeres.2008.03.002, vol. 27, No. 4, Jul. 1, 2008, pp. 464-499, XP023611418 ISSN: 1350-9462 [retrieved on Mar. 28, 2008] the whole document in particular chapter 2.3 and chapter 8.1.

A.Gh. Podoleanu and D.A. Jackson, "Combined Optical Coherence Tomograph and Scanning Laser Ophthalmoscope," *Electronics Letters*, vol. 34 No. 11 (May 28, 1998) (2 pgs.).

Roach et al., "Retinal Response of *Macaca mulatta* to Picosecond Laser Pulses of Varying Energy and Spot Size," *Journal of Biomedical Optics*, in press. vol. 9, No. 6 (2004) pp. 1288-1296. (9 pgs.).

Roorda et al., "Adaptive Optics Scanning Laser Ophthalmoscopy," *Optics Express*, vol. 10, No. 9 (2002) pp. 405-412. (8 pgs.).

* cited by examiner

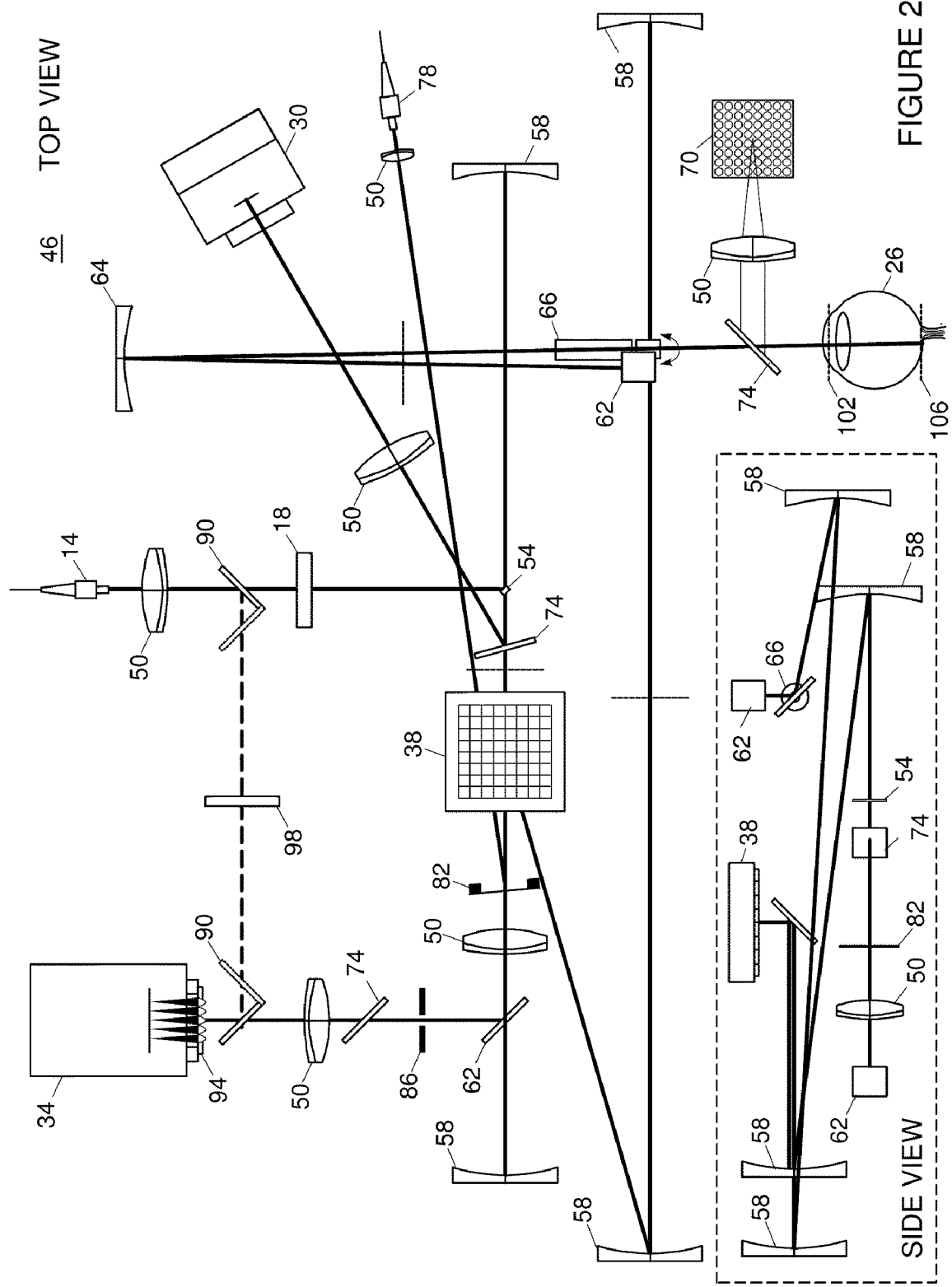

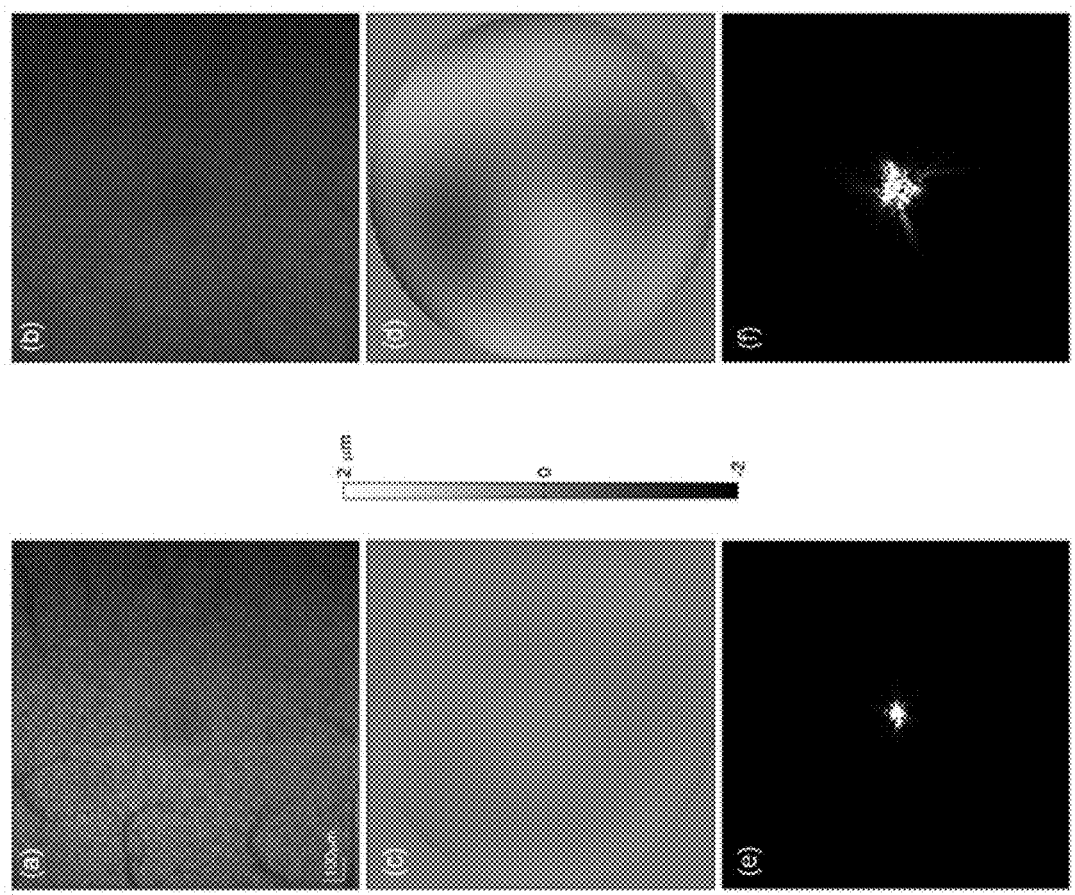
Figures 4A-F

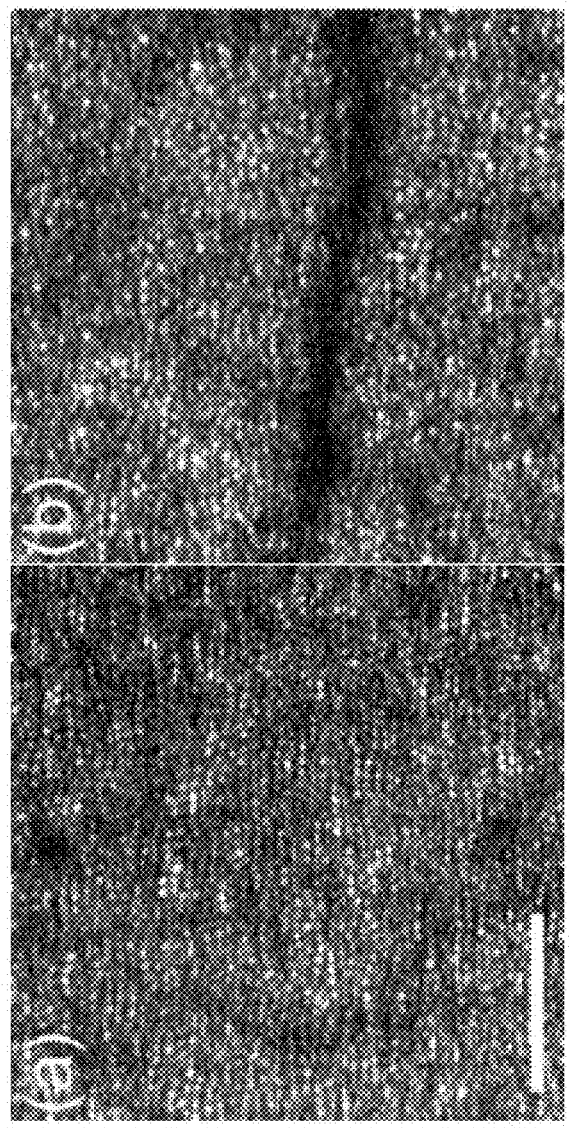
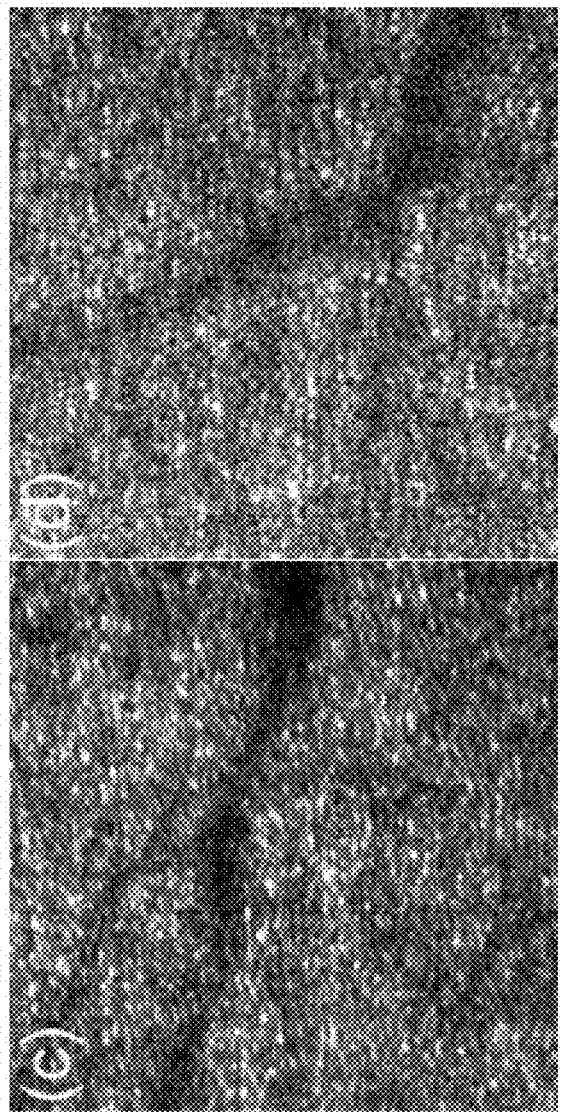
Figures 5A-D

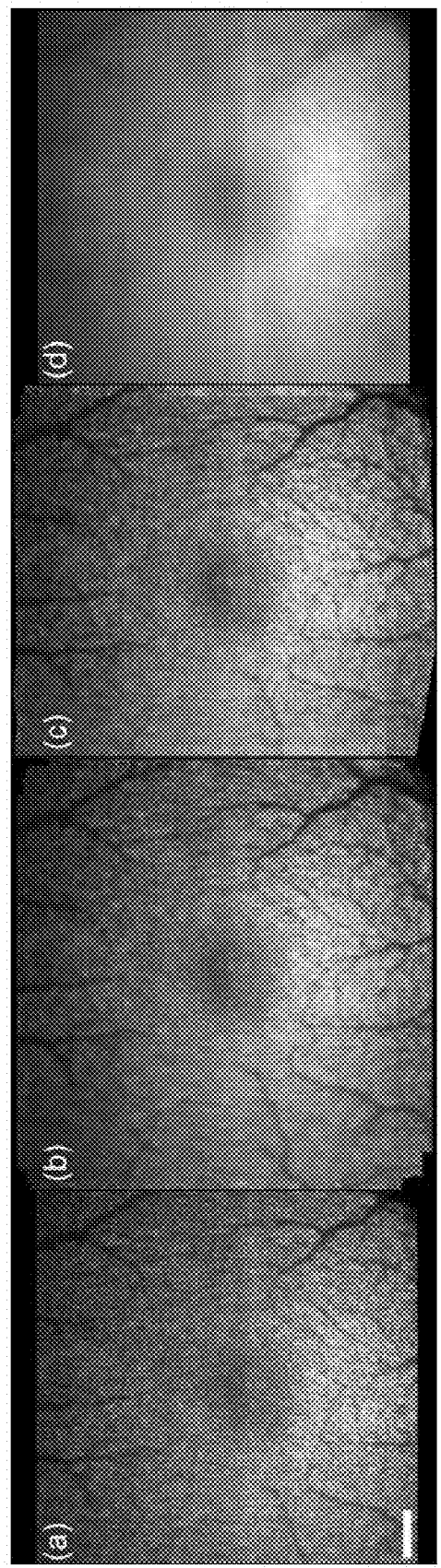
Figures 13A-D

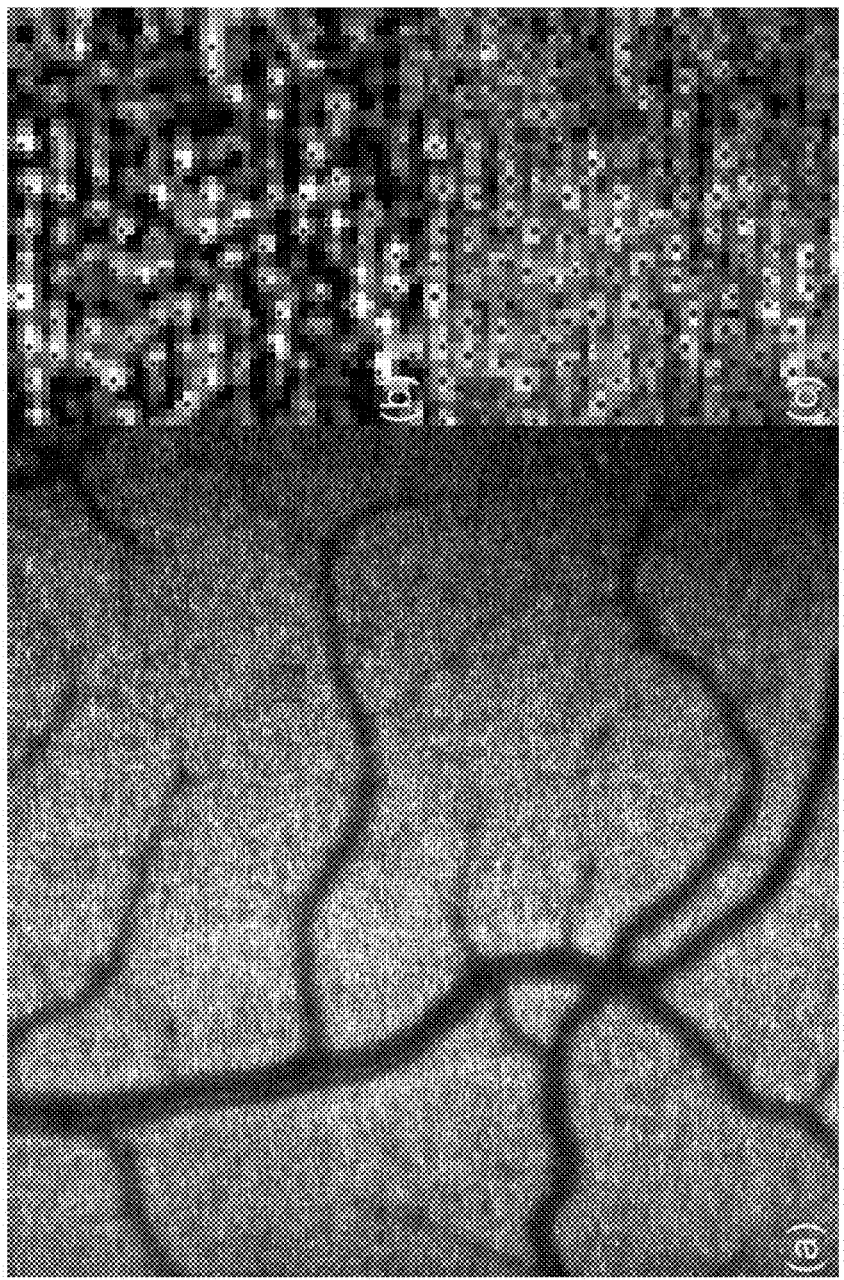
Figure 14A-C

ADAPTIVE OPTICS LINE SCANNING OPHTHALMOSCOPE

CROSS-REFERENCE TO RELATED APPLICATION

This application claims the benefit of and priority to U.S. provisional patent application No. 61/144,951 filed Jan. 15, 2009, which is owned by the assignee of the instant application and the disclosure of which is incorporated herein by reference in its entirety.

GOVERNMENT SUPPORT

The invention was made with government support under NIH National Eye Institute grant R43 EY018509. The government may have certain rights in the invention.

FIELD OF THE INVENTION

The invention relates generally to a method and apparatus for retinal or ocular imaging, and more particularly to a method and apparatus for correcting distortions in an optical image of an object (e.g., an eye).

BACKGROUND

A confocal imaging system (e.g., scanning laser opthalmoscope, confocal microscope, etc.) rejects light scattered from adjacent or out-of-plane voxels by use of a pinhole in front of the detector conjugate to the focal plane. This can improve image contrast and resolution over flood illumination and detection schemes. The line scanning approach multiplexes the illumination and detection in one dimension, while rejecting scattered light outside of the confocal range gate defined by the pixel size in a similar fashion as a flying-spot SLO.

Adaptive optics (AO) can be used as a tool to understand the structural and functional aspects of vision, the elegant but complex retinal circuitry, and the dissolution of that structure, wiring and processes during the execrable progression of disease. AO systems can sense ocular aberrations that arise primarily from the tear film, cornea, and lens with a wavefront sensor, and can corrects aberrations in a closed-loop manner with a wavefront compensator. A Hartmann-Shack wavefront sensor comprised of a lenslet array and CCD camera is typically used for rapid detection of ocular aberrations; however, other techniques such as interferometry can also be used. There are several methods to achieve wavefront correction including MEMS-based deformable mirrors, magnetic actuator deformable minors, and liquid crystal phase modulators.

AO can overcome limitations imposed by ocular geometry and optics. AO has enabled high lateral resolution imaging for clinical applications such as early detection, disease diagnosis and progression tracking. AO can be used as a tool to understand the structural and functional aspects of vision. These vision studies typically use improved imaging performance and some also benefit from improved ability to stimulate and probe retinal function. AO can also be used to guide therapies, for new drug discovery, and for the evaluation of therapeutic effectiveness. With AO, the fundamental level of information and detail that can be extracted from an eye is markedly improved.

The eye can essentially produce a nearly diffraction-limited retinal spot for a small pupil diameter less than approximately 2 mm. The eye has a numerical aperture (NA) of about 0.05 in this case and produces spots of 5 µm-10 µm for near-infrared light. However, as the pupil diameter is increased, ocular aberrations negate any gains from increased numerical aperture and the retinal spot size is essentially unchanged. A conventional confocal microscope can achieve sub-micron lateral ($\propto 1/NA$) and axial ($\propto 1/NA^2$) resolution with the use of high numerical aperture (NA) objectives. In opthalmology, imaging the posterior segment is limited by the NA and aberrations of the eye (~0.2 for a dilated pupil). Scanning laser opthalmoscopes (SLOs) are confocal instruments that block light scattered from other retinal lateral positions and depths that are not conjugate to a detector pinhole. They can achieve a lateral and axial resolution of approximately 5 µm-10 µm and 300 µm, respectively. The axial depth-of-focus for confocal instruments is often called the confocal range gate. AO can be used to correct ocular aberrations to achieve the true NA potential of a dilated eye. Adaptive Optics Scanning Laser Opthalmoscopes (AOSLOs) can achieve nearly diffraction limited spots (about 2.5 µm) and excellent optical sectioning (as low as 70 µm).

There are currently two barriers to widespread use of AO by clinicians and research scientists. The first barrier is the high cost of deformable mirrors. The second barrier is system complexity. Currently, AO systems can be built and operated only by researchers with extensive expertise in optics, engineering, and instrumentation. AO systems have been designed and constructed for the best imaging performance possible, to the exclusion of all other factors (size, cost, complexity, ease-of-use, etc.). This has slowed the transition of AO from the research lab to the clinic.

SUMMARY OF THE INVENTION

The invention, in one embodiment, features adaptive optics (AO) integrated into a line scanning opthalmoscope (LSO). The invention fills the niche between SLO instruments that provide wide field but limited resolution for routinely clinical use and the complex, high resolution, high-performance AO instruments. A compact, simplified AO instrument like the AO-LSO, which can be used by ophthalmologists, optometrists, and vision scientists, can advance the understanding of vision and the development of new techniques to detect and treat retinal diseases.

An AO-LSO can provide lateral resolution sufficient to visualize the cells and structures critical for vision. An AO-LSO has simplied optics, high-speed scanning components, and smaller footprint compared to a traditional research AOSLO. An AO-LSO can be used to visualize, for example, photoreceptors, fine capillaries, nerve fiber bundles, and drusen, new vessel growth, and lesions in a diseased eye. This advance in compact and lower-cost instrumentation can allow for more rapid transition of high resolution AO capabilities to routine clinical use to provide efficient and rapid image acquisition, early disease screening and detection, and enhanced diagnostic yield, and can guide existing and new treatment strategies. The capability to map and visualize retinal structures in unprecedented detail can improve the understanding of disease processes and improved treatment modalities.

A bench-top AO-LSO instrument can produce high resolution retinal images with only one moving part, a smaller instrument footprint, and fewer of optical components. The AO-LSO can have a moderate field of view (e.g., about 5.5 deg), which allows montages of the macula or other targets to be obtained quickly and efficiently. For example, the entire macular can be rapidly mapped with a 3×3 image montage. Photoreceptors can be resolved and counted within about 0.5 mm of the fovea. The capillaries surrounding the foveal avascular zone can be resolved, as well as cells flowing within them. Individual nerve fiber bundles can be resolved, especially near the optic nerve head, as well as other structures such as the lamina cribrosa. In addition to instrument design, fabrication, and testing, software algorithms can be used for automated image registration, cone counting, and montage stitching.

Adaptive optics components and a confocal line-scanning (also called line-field) retinal imaging approach (e.g., an AO-LSO system) can provide a reduction in hardware complexity by elimination of a high-speed scanner and associated mirror or lens relays. Lateral resolution and depth sectioning of the confocal line scanning approach can be improved with adaptive optics. For example, about 6-µm diameter photoreceptors can be resolved at eccentricities of about 0.6 µm (e.g., about 2 deg.). About 15-20 µm diameter nerve fiber bundles can be resolved in the nerve fiber layer. The system can resolve fine capillaries surrounding the foveal avascular zone and can visualize the vacuoles in the lamina cribrosa in the optic nerve head. In some embodiments, retinal images can be stitched to map the photoreceptor mosaic across the entire macula (e.g., about 15 deg.). Acquisition software can be used to control and synchronize instrument hardware, including the deformable mirror, Hartmann-Shack wavefront sensor (HS-WS), galvanometer, and linear detector. In some embodiments, analysis software is used for automated registration and averaging, cone counting, and generation of montages. In some embodiments, the system includes a high-stroke deformable mirror, only one moving part, half the optical elements (e.g., spherical minors) of a traditional AOSLO setup, and can feature further reduction in hardware.

The AO-LSO system can include the use of wavefront sensorless AO control algorithms adapted to the line scanning retinal imager. Wavefront sensorless algorithms can extract information on ocular aberrations from the image information itself, rather than from a separate wavefront sensor. The algorithm can process image information efficiently enough to operate in real time (e.g., at about 10 Hz), and can obviate the need for a separate wavefront sensor, resulting in further reduction in system complexity. With implementation of a wavefront sensorless algorithm, the AO-LSO system can include (e.g., can be reduced to) a deformable mirror, a linear detector, a galvanometer, and a spherical mirrors. The implementation of a wavefront sensorless algorithm, therefore, not only decreases the cost to produce a device, but also enables a less complex, easier to operate instrument.

Acquisition and analysis software can be used for streamlined and rapid information collection and automated analysis. The output of this analysis can be in the form of disease customized reports with information on, for example, photoreceptor density maps across retinal patches that include margins of geographic atrophy, the average size and overall coverage of macular drusen, and the diameter and density of new vessels within choroidal neovascular lesions. Overall global retinal health can also be presented to the clinician with statistics on retinal flowmetry.

In one aspect, the invention features an apparatus that includes a first optical module that (i) scans a portion of an eye with a line of light, (ii) descans reflected light from the scanned portion of the eye and (iii) confocally provides output light in a line focus configuration. The apparatus also includes a detection device that detects the output light and images the portion of the eye. The apparatus includes a second optical module that (i) detects an optical distortion and (ii) corrects the optical distortion in the line of light scanned on the portion of the eye.

In another aspect, the invention features a method for imaging a portion of an eye. The method includes scanning a portion of an eye with a line of light and descanning reflected light from the scanned portion of the eye. The method also includes confocally providing output light in a line focus configuration to a detector and imaging, with the detector, the portion of the eye from the output light. The method also includes detecting an optical distortion and correcting the optical distortion in the line of light scanned on the portion of the eye.

In another aspect, the invention features a method for imaging a portion of an eye. The method includes imaging a portion of an eye with a line of light, detecting an optical distortion in an image of the portion of the eye and correcting the optical distortion in the light of light that images the portion of the eye.

In yet another aspect, the invention features an apparatus that includes a line scanning opthalmoscope, a first module that detects an optical distortion and a second module that corrects the optical distortion in a line of light of the line scanning opthalmoscope that images a portion of an eye.

In another aspect, the invention features a method for registering an image from a line of light. The method includes choosing, by a computing device, a key frame in the image from the line of light and identifying, by a computing device, similar structural features in the key frame and at least one other frame in the image from the line of light. The method also includes aligning, by a computing device, the at least one other frame to the key frame to register an image from the line of light.

In yet another aspect, the invention features a method for counting cones in an image of an eye. The method includes correcting for, by a computing device, a non-uniform image background in the image from the line of light and subtracting, by a computing device, the background and enhance the image from the line of light. The method also includes identifying, by a computing device, regions with local maxima to obtain an estimate of each cone location based on a centroid of the region.

In still another aspect, the invention features an apparatus comprising a source of optical radiation and a cylindrical lens configured to receive the optical radiation and to form the optical radiation into a line of light. An optical system includes a scanner and at least one focusing element. The scanner is configured to scan a portion of an eye with the line of light and to descan reflected light from the portion of the eye. The scanner and at least one focusing element are configured to confocally provide output light in a line focus configuration. A linear array detector is configured to detect the output light in the line focus configuration and to image the portion of the eye. A wavefront sensor is adapted to detect an optical distortion, and a wavefront compensator is adapted to correct the optical distortion in the line of light scanned on the portion of the eye.

In other examples, any of the aspects above, or any apparatus or method described herein, can include one or more of the following features.

The second optical module can detect an optical distortion from an image from the detection device. In some embodiments, the second optical module includes a wavefront sensor that detects the optical distortion and a wavefront compensator that corrects the optical distortion in the line of light scanned on the portion of the eye. The second optical module can include a deformable mirror that corrects the optical distortion in the line of light scanned on the portion of the eye.

In some embodiments, the detection device is a linear array detector. At least one optical relay can be used to direct the line of light to the deformable minor.

The first optical module can include a light source and a first optical component that receives light from the light source and provides the line of light. The second optical module can include a second light source and a second optical element that allows a portion of the light from the second source to pass. In some embodiments, the second optical element includes a pellicle beamsplitter, dichroic beamsplitter, or any combination thereof.

The optical distortion can be detected from an image from the detection device. At least one image from the line of light can be processed to detect the optical distortion. Light from a second light source can be used to detect the optical distortion. In some embodiments, a wavefront sensor can detect the optical distortion and a wavefront compensator can correct the optical distortion. A portion of the eye can be imaged to a wavefront sensor to detect the optical distortion. An adaptive optical element can be used to compensate for the optical distortion. In some embodiments, a deformable minor is used to correct the optical distortion in the line of light scanned on the portion of the eye.

In some embodiments, an apparatus includes a line scanning opthalmoscope and a module that includes a wavefront compensator that corrects the optical distortion in the line of light. In some embodiments, the module includes a wavefront sensor that detects the optical distortion from a beam of light. The wavefront compensator can be a deformable minor. The module can include a processor in communication with the module. The processor can determine the optical distortion based on at least one image from the line of light.

In some embodiments, the invention features an apparatus that includes a single light source that directs light to an optical component that provides the line of light. The apparatus can include a single detection device that images a portion of an eye.

In some embodiments, a second module is tangibly embodied in electronic circuitry or computer readable medium and the second module is configured to register an image from the line of light, count cones in an image from the line of light, or any combination thereof. The second module can be configured to choose a key frame in the image from the line of light, identify similar structural features in the key frame and at least one other frame in the image from the line of light and align the at least one other frame to the key frame to register an image from the line of light. The second module can also be configured to correct for a non-uniform image background in the image from the line of light, subtract the background and enhance the image from the line of light and identify regions with local maxima to obtain an estimate of each cone location based on a centroid of the region.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 2 shows an illustrative embodiment of an AO-LSO system in top view and side view.

FIGS. 4A-4H show an example of AO correction.

FIG. 5A-5D show examples of the photoreceptor mosaic imaged at various eccentricities for four subjects.

FIGS. 13A-D depict a comparison of registration techniques.

FIGS. 14A-C show a comparison between manual and automated cone counting at an eccentricity of 0.8 mm.

DESCRIPTION OF THE INVENTION

Figure 1:
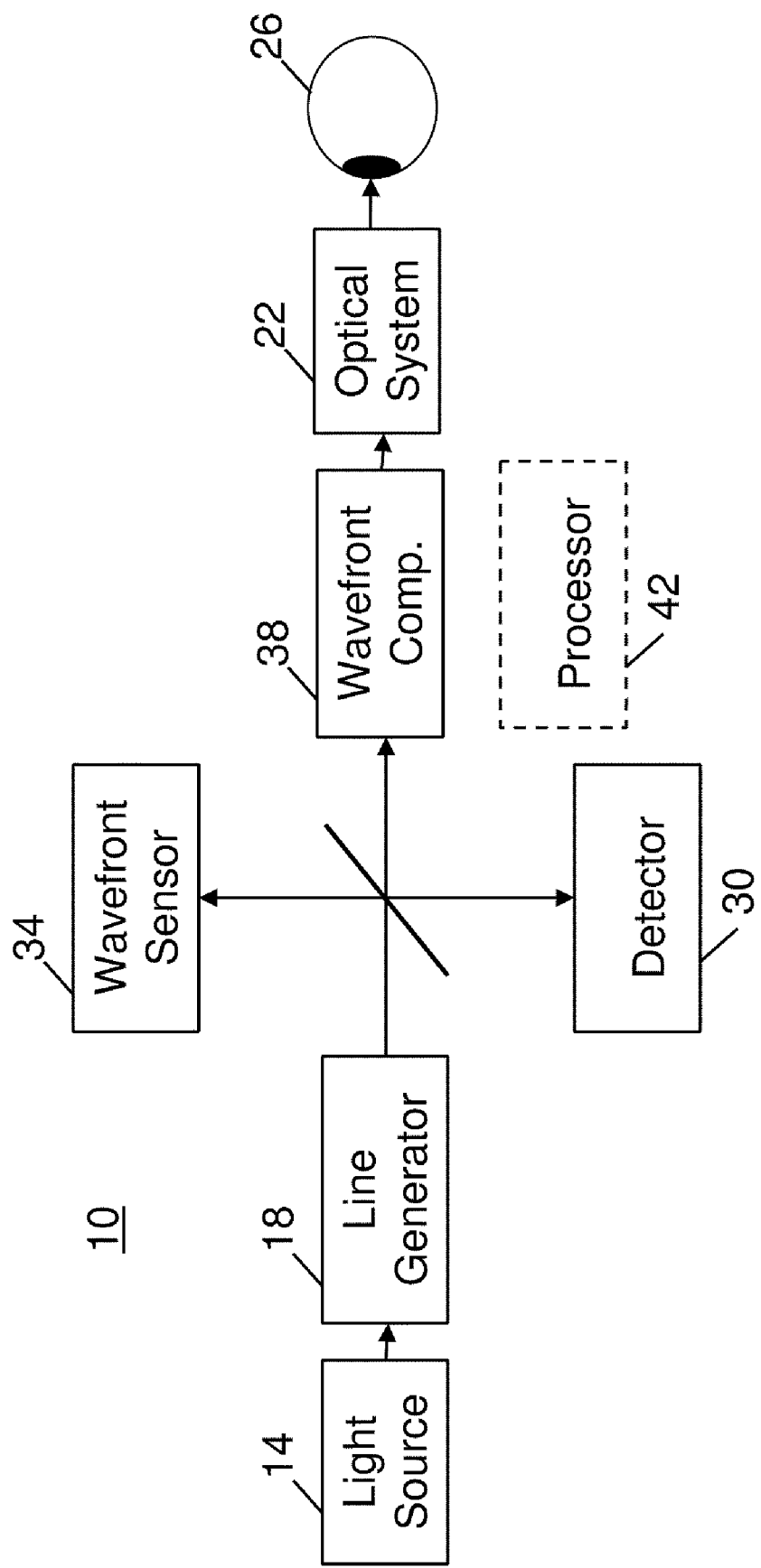
FIG. 1 shows an optical apparatus according to the invention.

FIG. 1 shows an optical apparatus 10 including a source 14 of optical radiation and a line generator 18 (e.g., a cylindrical lens) configured to receive the optical radiation and to form the optical radiation into a line of light. An optical system 22 (e.g., a first optical module) includes a scanner and at least one focusing element (e.g., one or more mirrors, one or more spherical minors, one or more parabolic mirrors, one or more lens, or any combination of the aforementioned). The scanner is configured to scan a portion of an eye 26 with the line of light and to descan reflected light from the portion of the eye. The scanner and the at least one focusing element are configured to confocally provide output light in a line focus configuration. A linear array detector 30 is configured to detect the output light in the line focus configuration and to image the portion of the eye. A wavefront sensor 34 is adapted to detect an optical distortion, and a wavefront compensator 38 is adapted to correct the optical distortion in the line of light scanned on the portion of the eye. The optical apparatus 10 can include a processor 42, which can be in communication with at least one of the source 14, optical system 22, linear array detector 30, wavefront sensor 34, or wavefront compensator 38.

FIG. 2 shows an illustrative embodiment of an AO-LSO system 46 in top view and side view. The optical components for the AO-LSO system 46 are compact and designed to fit on a plate (e.g., such as a 8×24 inch (45×60 cm) or 12×18 inch (30×45 cm) plate/optical breadboard) that can be mounted to a standard slit lamp stand (e.g., or other joystick operated housing). In some embodiments, the AO-LSO system 46 includes spherical mirrors with smaller radii of curvature in a compact folded optical path. The AO-LSO system can be housed in a portable package suitable for clinical use.

The AO-LSO system 46 includes a source 14 of optical radiation, a cylindrical lens, six lenses 50, a beam pick-off 54, four out-of plane spherical mirrors 58, three turning minors 62, a fifth spherical mirror 64, wavefront compensator 38 (e.g., a deformable mirror), a scanner 66, fixation target 70 for eye 26, three dichroic beamsplitters 74, a second light source 78, a pellicle beam splitter 82, iris aperture 86, a pair of flip mirrors 90, a wavefront sensor 34 including a lenslet array 94, and a neutral density filter 98. Wavefront compensator 38, scanner 66, and lenslet array 94 are placed at the pupil conjugate 102, and detector 30 and wavefront sensor 34 are placed at the retinal conjugate 106.

The four out-of plane spherical minors 58 can serve as two optical relays to transfer the pupil to the wavefront compensator, e.g., a large-stroke deformable mirror (e.g., a Mirao deformable mirror available from Orsay, France, Imagine Eyes, Inc.) and to the scanner 66 (e.g., a single imaging galvanometer). The scanner can pivot about the pupil to scan a line of light across a small patch of retina. The fifth spherical minor 64 can perform an f-2f transform between relays.

Although the system and optical relays are described with spherical minors as the focusing elements, other focusing elements such as other types of minors including parabolic minors, one or more lenses, or any combination of the aforementioned can be used. Spherical minors produce no back-reflections and can reduce overall system aberration. The angles between the spherical mirrors can be kept small to minimize astigmatism. The magnification of the relays can be constrained in the design by the wavefront compensator diameter (about 15 mm), the linear array detector (Aviiva SM2 CL, e2v Inc. Chelmsford, England) length (about 10.24 mm), and the desired input beam diameter at the pupil. The input beam diameter can be set to 7.5 mm to achieve high lateral resolution for a dilated pupil with minimization of ocular aberrations. The magnification from the detector to the retina can be about 6.4. The field size on the retina can be 1.6 mm (5.5 deg for an emmetropic eye), and the pixel size of the retinal images can be about 1.56 µm. The overall pathlength can be relatively long (about 2.6 m from illumination fiber to eye). However, the number of optical elements can be small. A high stroke deformable minor can reduce focal lengths and folding for increased compactness. In addition to wavefront correction, instrument focusing (de-focus correction) can be performed with the deformable mirror.

The optical source 14 can be a coherent source, such as a laser, or a incoherent source, such as a diode or a lamp. In certain embodiments, optical source 14 is a dual superluminescent diode (SLD) source with a bandwidth of about 65 nm and a center wavelength of about 820 nm (Broadlighter, Superlum Inc., Carrigtwohill, Ireland). The optical source can be fiber coupled to the optical apparatus, and can be used for illumination to eliminate coherent speckle. The illumination beam can be spread in one axis with a cylindrical lens and transferred via the optical relays to the wavefront compensator and the scanner, where it can be scanned in the other axis to produce a raster on the retina. The raster light returned from the retina can be de-scanned with the scanner, and the fixed line can be passed back though the system and focused on the detector to produce retinal images.

The second optical source 78 can be a separate beacon (e.g., a 735-nm laser diode) used to sense aberrations. The second optical source can be introduced with the pellicle beamsplitter 82 and dichroic beamsplitter 74 (D2). The pellicle can be used to pick off a portion (e.g., about 8%) of the 735 nm beacon light available at the input and to maximize return signal. The dichroic beamsplitter can be cut for efficient separation of imaging and beacon light (e.g., greater than about 95% transmission at 735 nm and greater than about 90% reflection at 820 nm). The beacon can be parfocal and paraxial to the imaging beam from the first source 14. An additional lens relay can be used to de-magnify the return beacon light to 7.5 mm on the wavefront sensor, e.g., a Hartmann-Shack wavefront sensor (HS-WS) (available from Uniq Inc., Santa Clara, Calif.). The iris 86 can block light from corneal reflections from corrupting the HS-WS images. The HS-WS and the detector can be synchronized to the same fsync signal to provide for aberration correction of the same retinal patch. In some embodiments, the system can implement wavefront sensor-less control algorithms for decreased device complexity. Two flip-mounted mirrors 90 can be used for HS-WS calibration using the imaging beam from the first source 14. With low system aberrations, this calibration can be performed at other retinal conjugates.

In some embodiments, the linear detector 30 can be a high speed detector (e.g., 70 kHz line rates) that produces high resolution (2048 pixels across similarly sized retinal fields) images. A high frame rate operation can allow a larger number of images to be collected in shorter sessions. The system can be used to investigate, for example, retinal hemodynamics.

A subject's head and eye can be stabilized with a bite bar, forehead rest and a fixation target 70. A cold mirror can be used to transmit imaging and beacon beams while reflecting the fixation target into the eye. The fixation target can be a computer-controlled 8×8 LED array or high resolution liquid crystal display.

Processor 42 can run AO-LSO acquisition and control software. The AO components (e.g., the wavefront sensor and the wavefront compensator) and the imaging components (LSO and detector) can be controlled from two separate (but linked) programs. The AO control software can acquire images from the wavefront sensor camera and calculate the correction voltages to apply to the wavefront compensator (e.g., to the deformable mirror actuators). The AO control software can also be responsible for AO calibration, setup and control of all camera and image acquisition (i.e., framegrabber) parameters, and real-time computation of wavefront error maps and Zernike coefficients. The LSO imaging software can acquire and save images from the linear detector. The LSO imaging software can also be responsible for fixation target control, and setup and control of the camera and image acquisition (i.e., framegrabber) parameters, including synchronization between the wavefront sensor and the detector.

Figure 3A:
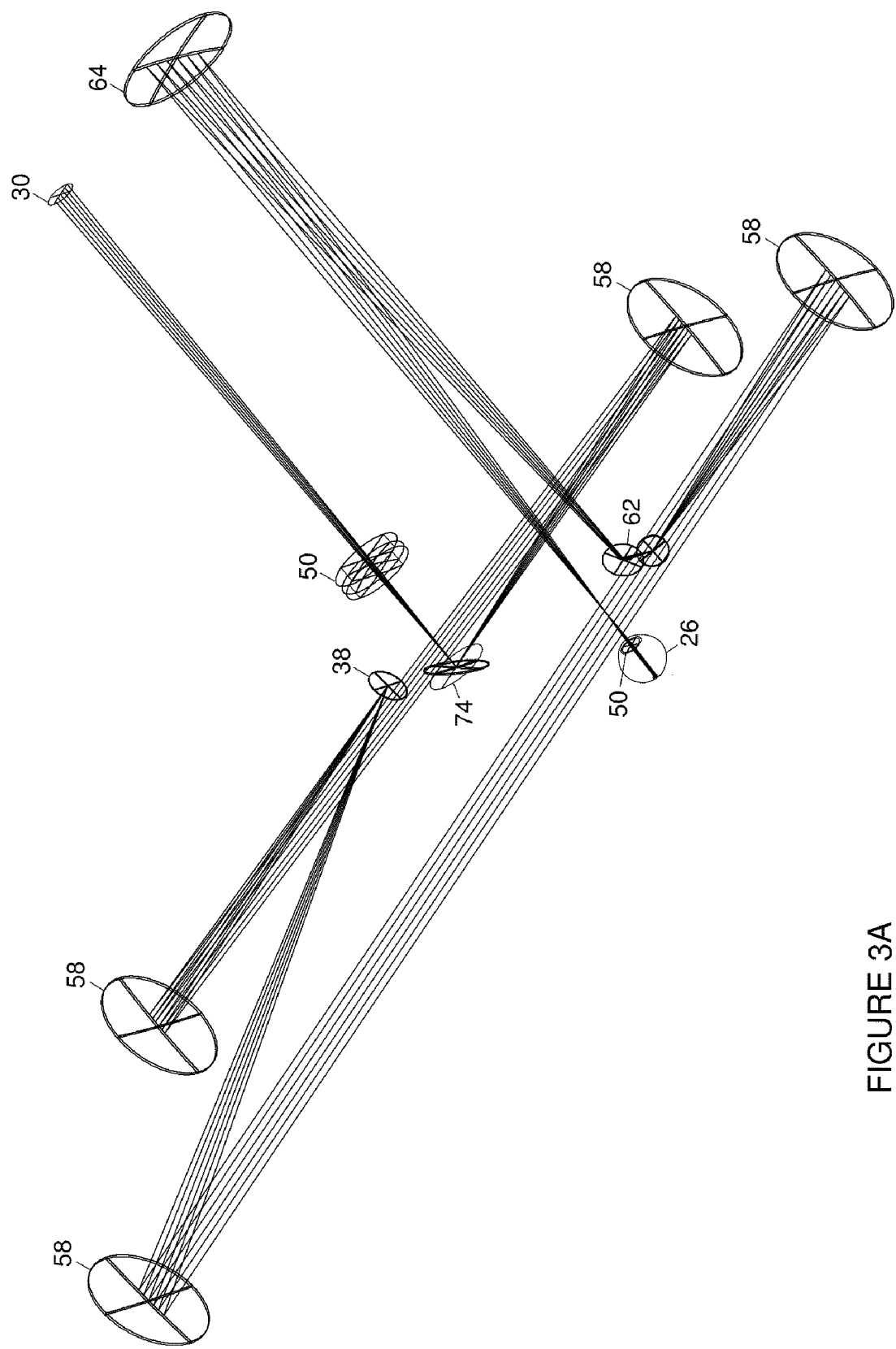
FIG. 3A depicts an optical layout of an AO-LSO.
Figure 3B:
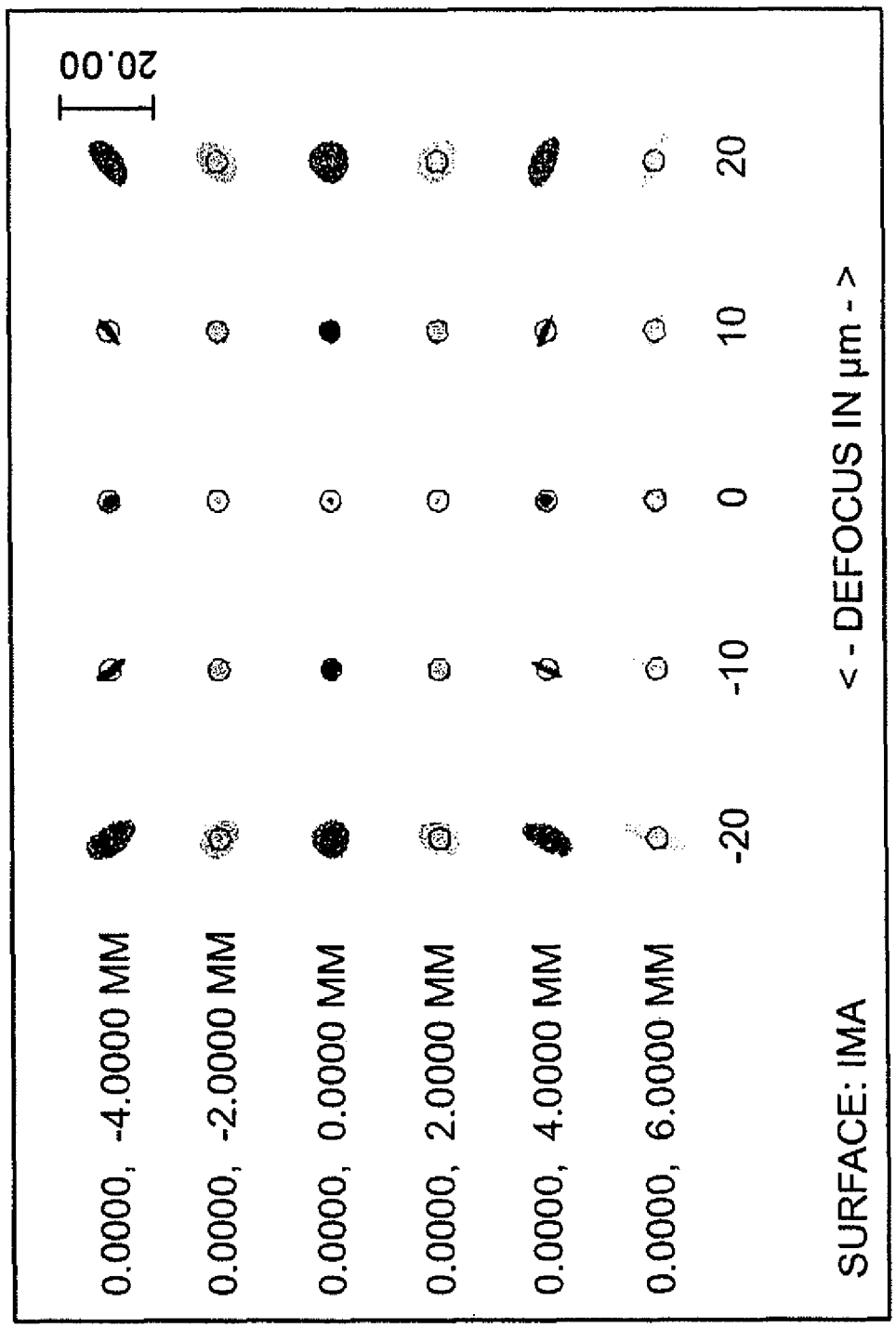
FIG. 3B shows a through-focus spot diagram for the AO-LSO of FIG. 3A.

FIG. 3A shows an optical layout of an AO-LSO, and FIG. 3B shows a through-focus spot diagram for the AO-LSO of FIG. 3A. In this embodiment, the wavefront sensor is not shown in the optical layout. The through-focus spot diagram shows diffraction-limited performance on axis (third row down) and some astigmatism off-axis (rows 1, 2, 4, 5, and 6) present in the system without AO compensation.

The line scanning approach is normally configured for wide-field retinal imaging. The image resolution of the instrument can be determined by the pixel size (projected onto the retina) and the Airy disc of the input beam. The Nyquist limit can define a factor of 2 for the maximum pixel sampling of the Airy disc (which should be nearly diffraction-limited with AO). The pixel size can be also constrained by light collection efficiency adjacent to the line. The AO-LSO can be constrained physically and optically by the size of the deformable mirror and the size of the linear detector. Thus, the Airy disc and the pixel size cannot be made arbitrarily small, even though some linear detectors exist with very small pixels.

To configure the line scanning approach for high resolution small field imaging, a trade-off between the optical performance and the light collection efficiency for a moderately sized linear detector pixel (10 µm) can determine the resolving power of the instrument. The field size on the retina can be designed to be about 5.5 deg. and the de-magnified pixel can be about 1.5 µm (e.g., 1024 pixels). A Zemax optical model indicates that diffraction-limited performance within an Airy disc radius of about 2.4 μm (820 nm) can be achieved in a paraxial eye with aberration correction using only a small fraction of the deformable mirror dynamic range. Residual off-axis astigmatism can be corrected by the deformable mirror.

The system was tested with human subject investigations. The system was initially tested in a limited number of human subjects without retinal disease. Ten subjects (7 male, 3 female) with an average age of 47 years were imaged. 3 subjects were myopic, 4 subjects were emmetropic (visual acuity 20/40 or better), 4 subjects were hyperopic, and 6 subjects were presbyopic. The average refractive error was approximately −5.0 D for the myopes and +1.5 D for the hyperopes. No subject's eyes were dilated during the investigation. However, most subjects had at least 4-5 mm diameter pupils, which was amenable to lateral resolution and depth sectioning improvement from AO compensation. The room was darkened and a baffle was used to provide dark-adapted pupil dilation. Some subjects had 7-8 mm pupils when not looking directly at the NIR beacon and illumination beams. The pupils constricted when imaging the fovea. Irregular pupil dilation accounted for some of the variability seen in resultant imaging performance and also accounted for the relatively smaller differential in AO correction (as measured by $\Delta[\text{wavefront error}]_{RMS}$) for images collected from the fovea.

A wax impression bite bar and forehead rest were used for head stabilization and pupil centration. The central macula was the image target in most individuals, although in some subjects, the optic nerve head was also imaged. Photoreceptors were resolved in all subjects except two, one of which had a mild cataract. The deformable mirror was able to statically correct de-focus (prior to AO compensation) in all individuals. LSO and HS-WS videos with a duration of 5-30 seconds were acquired.

Figure 4G:
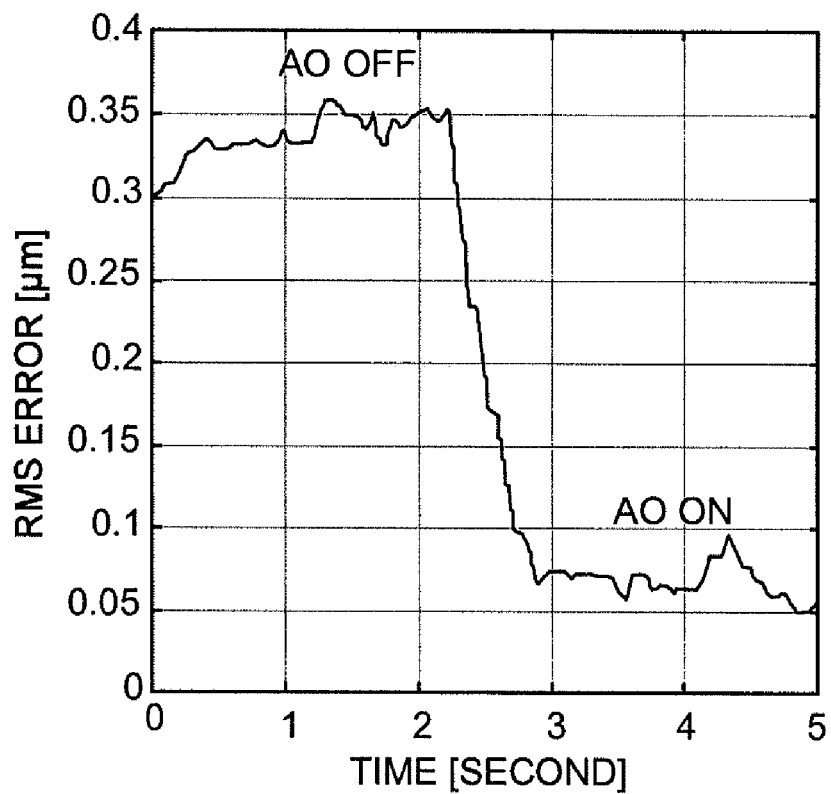

Adaptive optics dynamically corrected the input wavefront for ocular aberrations and improved the lateral resolution in LSO images collected from human subjects. FIGS. 4A-4H show an example of AO correction. FIGS. 4A, 4C, and 4E show a single LSO image, average wavefront error map, and average point spread function, respectively, with AO correction, and FIGS. 4B, 4D, and 4F show the same without AO correction.

Figure 4H:
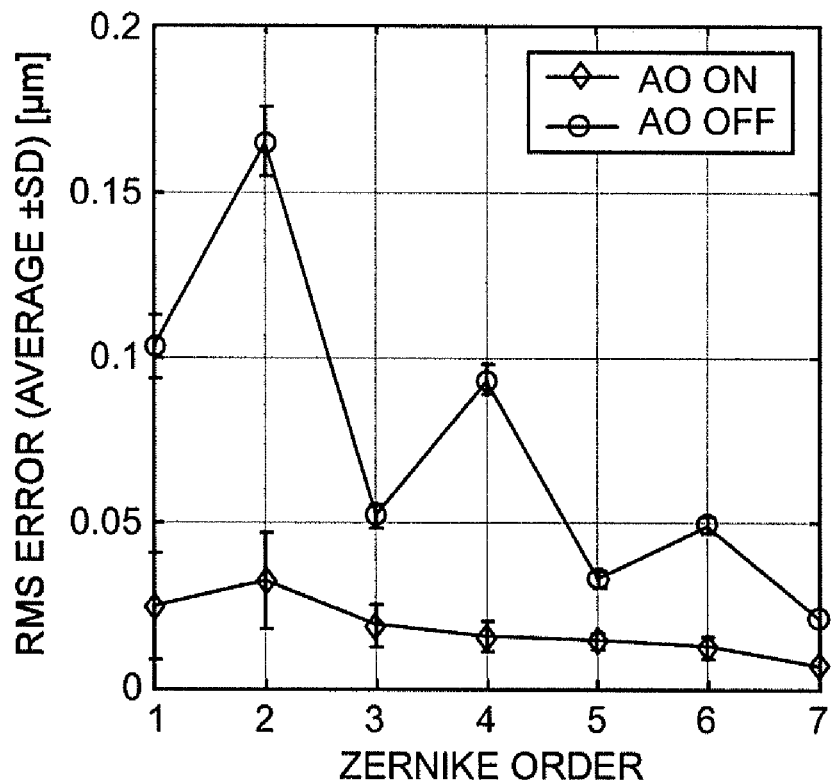

FIG. 4A shows an LSO images acquired with AO correction. FIG. 4B shows an LSO images acquired without AO correction. FIG. 4C shows a wavefront error map with AO correction averaged over an about two second duration for an 8-mm pupil. FIG. 4D shows a wavefront error map without AO correction averaged over an approximately two second duration for an 8-mm pupil. FIG. 4E shows a point spread function with AO correction averaged over approximately a two second duration. FIG. 4F shows a point spread function without AO correction. FIG. 4G shows the time-course of the RMS wavefront error for frames with and without AO correction. FIG. 4H shows RMS wavefront error by Zernike order for frames with and without AO correction. The full scale for the wavefront error map of FIG. 4G is ±2 μm. The LSO images in FIG. 4 are about 5.5 deg (1.6 mm).

The images acquired without AO correction had spherical correction applied to the deformable mirror to achieve the best possible focus correction. The average RMS error was 0.34 μm before correction (43 frames) and 0.07 μm after correction (48 frames). The Strehl ratio improved from $2.2 \times 10^{-4}$ to 0.70. Zernike orders up to 7 showed improvement, although the most improvement was seen in the first four orders. The 10-90% risetime for the correction was 0.52, for a closed loop bandwidth of about 2 Hz, slower than that achieved previously for other deformable mirrors. This is consistent with analysis that has shown that the Imagine Eyes deformable mirror has a slower response time (about 25 ms) than the response time for the Boston Micromachines Corp. (Cambridge, Mass.) BMC deformable minor (e.g., about 1 ms). The closed loop bandwidth can be faster with other mirrors or types of correction.

Photoreceptors were resolved in 80% of the individuals imaged in this small pilot proof-of-principal human subject investigation. Photoreceptors were resolved within about 0.3 mm (about 1.0 deg.) of the fovea for some individuals. According to previously reported histology, the cone size at this eccentricity is roughly equivalent to the size of 3 pixels for the AO-LSO instrument. Photoreceptors were reliably counted (e.g., manually) within about 0.5 mm to about 1 mm (i.e., about 1.5-3 deg.) for all subjects where they were resolved.

The photoreceptor mosaic was examined more thoroughly in 4 of 10 subjects. Three of these subjects were emmetropes and one had relatively large astigmatism (OS: −1.75 D/065, OD: −2.5 D/098). For these subjects, videos were acquired for generation of montages across the entire macula (central 15 deg.). Additional analysis included manual and automated cone counting and frequency analysis as a function of eccentricity.

FIG. 5A-5D show examples of the photoreceptor mosaic imaged at various eccentricities for four subjects. The scale bar is about 100 μm. FIGS. 5A and 5B show photoreceptors resolved at an approximate eccentricity of 0.76 mm. FIG. 5C shows photoreceptors resolved at an approximate eccentricity of 0.58 mm. FIG. 5D shows photoreceptors resolved at an approximate eccentricity of 0.72 mm.

Subject (a) appears to have a higher density of photoreceptors than subject (b) at roughly equivalent eccentricities. For good fixators (e.g., FIG. 5A), little distortion in individual photoreceptors is seen. For other subjects, intraframe distortions from microsaccades caused the cones to appear elongated (e.g., FIG. 5C).

In several individuals, short video clips (about 5 sec.) were collected while different fixation target LEDs were illuminated to move fixation to nine offset positions with respect to the imaging raster. These were used to map the photoreceptor mosaic across the entire macula. The best individual images from the videos (i.e., those with the best photoreceptor contrast and absent shear from saccades) were used to build up a montage of a region sized about 3.5-4.5 mm (about 12-15 deg.) depending upon overlap and the subject's ability to fixate. The images were aligned manually, where individual photoreceptors were matched in the overlap region. In some embodiments, software automatically stitches individual frames to generate the montage. If torsional eye motion and other sources of image warp are not corrected for, it can prevent perfect overlap of the individual frames.

Figure 6:
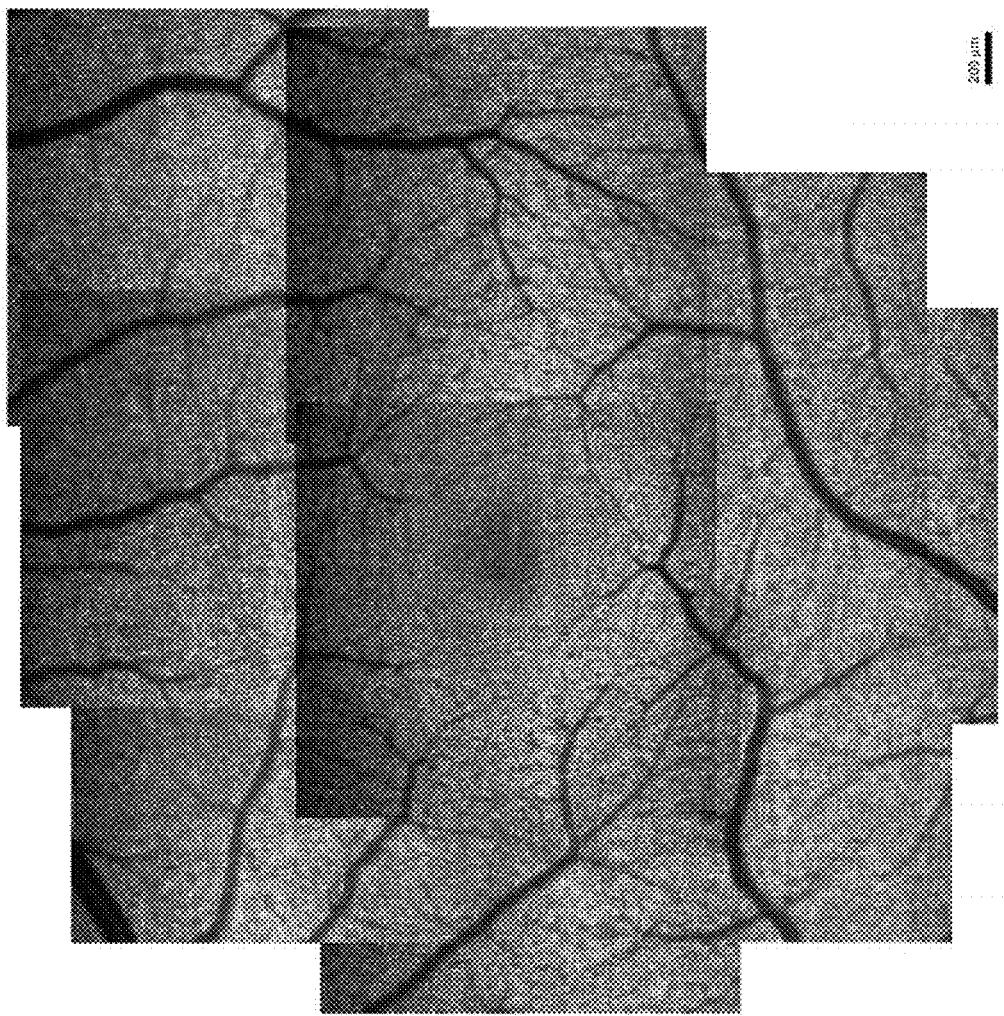
FIG. 6 shows a central macula montage of nine AO-LSO frames.

Generally, AO correction was left active (i.e., loop closed) while the fixation target LED was changed, and with slight adjustment of the beam to maintain pupil centration, the videos were collected in rapid sequence. In the four subjects where this sequence was performed, the imaging time to collect all the videos ranged from 8 to 18 minutes. In some embodiments, the technology features a scanning arrangement for automated montaging, which reduces the time to collect full macular montages (3×3 matrix) to about 20 seconds. To map a similar region of the retina with a research AOSLO with a field of view of about 1.5 deg. can require something on the order of 100 individual scans. FIG. 6 shows a central macula montage of nine AO-LSO frames.

Figure 7:
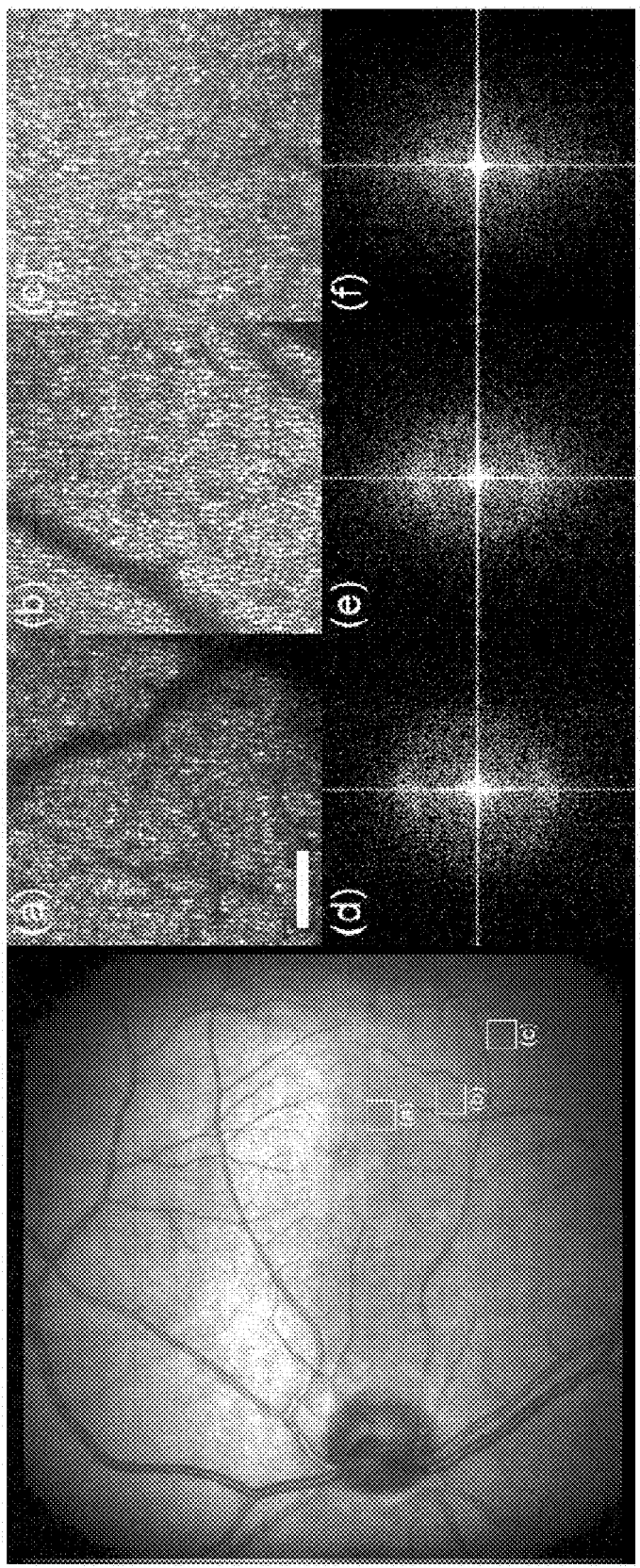
FIG. 7 shows the AO-LSO image and accompanying frequency maps for three regions at different eccentricities.

FIG. 7 shows the AO-LSO image and accompanying frequency maps for three regions at different eccentricities. FIGS. 7A-7C show cone mosaics, and FIGS. 7D-7F show frequency maps corresponding to the cone mosaics for retinal patches at eccentricities of (a) 0.83 mm (about 3 deg.), (b) 1.72 mm (about 6 deg.), and (c) 2.66 mm (about 9 deg.) as indicated on the wide field LSO image. The scale bar is about 100 μm.

The frequency maps show a ring corresponding to the photoreceptor density the diameter of which decreases (toward DC) as the photoreceptor spacing increases. The frequency content is used in the post-processing software to filter the images to achieve a more accurate cone count. The frequency maps can be created by applying a 2-D fast Fourier transform (FFT) to each image region and shifting the result so DC is in the center.

Figure 8:
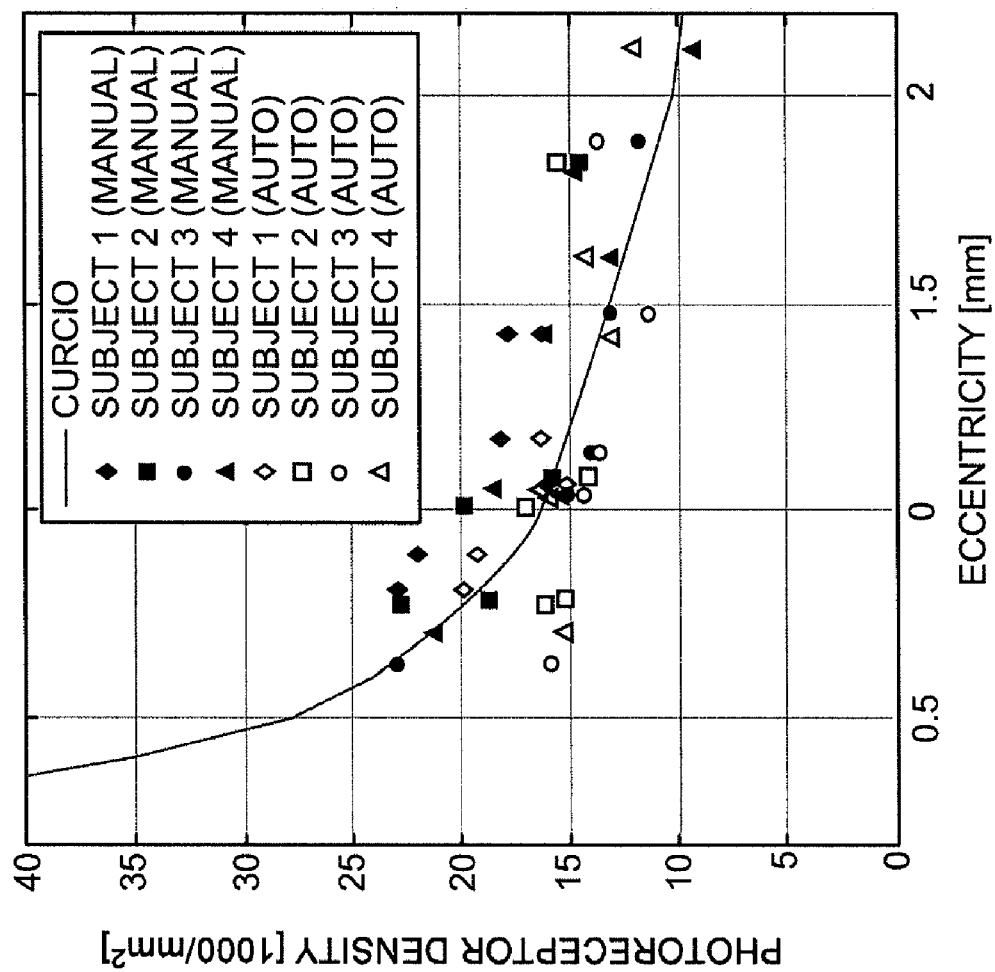
FIG. 8 depicts photoreceptor counts.

FIG. 8 shows photoreceptor counts in comparison to previously reported histology. Manual counts are shown with solid symbols and automated counts are shown with open symbols.

AO-LSO images from four subjects at various eccentricities (i.e., from 0.5-2.5 mm) were used for cone counting. A region sized 50×50 pixels (78×78 μm) was chosen where photoreceptor contrast was good and there was no (or very little) shadowing from overlying retinal capillaries. A software program (e.g., as part of the AO analysis software libraries) can be used to perform manual cone counting. The manual cone counting software allowed the user to click on the location of an individual cone, which immediately updated the image overlay with a mark indicating that the cone had been counted. When all the cones in a region were fully marked, the image with overlay and cone coordinates was saved. Automated cone counting software can also be used. The results from both manual and automatic counting are shown above in FIG. 8 in comparison to previously reported histology. Subject 1 generally had a higher cone density at all eccentricities. This subject is the same as that shown in FIG. 5A where a qualitatively high density was noted. The automated cone counts tended to be closer to histology for larger eccentricities and were inaccurate for the smallest eccentricities (less than about 0.8 mm). At this eccentricity, where the cone densities re greater than about 20,000/mm$^2$, the diameter of the average cone for the AO-LSO is about 4.5 pixels. In general, the manual and automated cone counts were reasonable well matched (less than about 20% difference between them 82% of the time), with the manual counts typically higher than the automated counts (77% of the time) and the largest differences occurring at the smallest eccentricities. For eccentricities greater than 0.8 mm, therefore, the automated software can be robust and accurate at counting cones.

There are several factors that can explain the differences between histology and both the manual and automated cone counts. The fact that the manual cone counts were higher can be explained by a number of factors. There is naturally a spread in cone densities across the entire subject population, and since 3 of the 4 subjects tested had very good vision, their densities may be slightly higher. Second, it is possible that the analyzer (the PI) incorrectly labeled regions cones that were not (false positive). It is possible that the automated software did not label regions cones that were (false negative). Third, it is possible that when choosing a sampling location, the analyzer chose a non-representative region where cones can be best visualized and thus artificially inflated the true cone density at that eccentricity. Differences in retinal sampling location (i.e., nasal, temporal, inferior, superior) were not distinguished. Differences exist between cone densities along the meridianal and equatorial directions which can account for some of the apparent fluctuations in measured cone densities as a function of eccentricity.

To examine flow in the finest retinal capillaries, the AO-LSO system focus was pulled forward (with the deformable mirror) to the inner retinal layers where the vessels reside (inner nuclear and inner plexiform layers). Flow was visualized in the smallest capillaries that form a ring around the foveal avascular zone.

Figure 9:
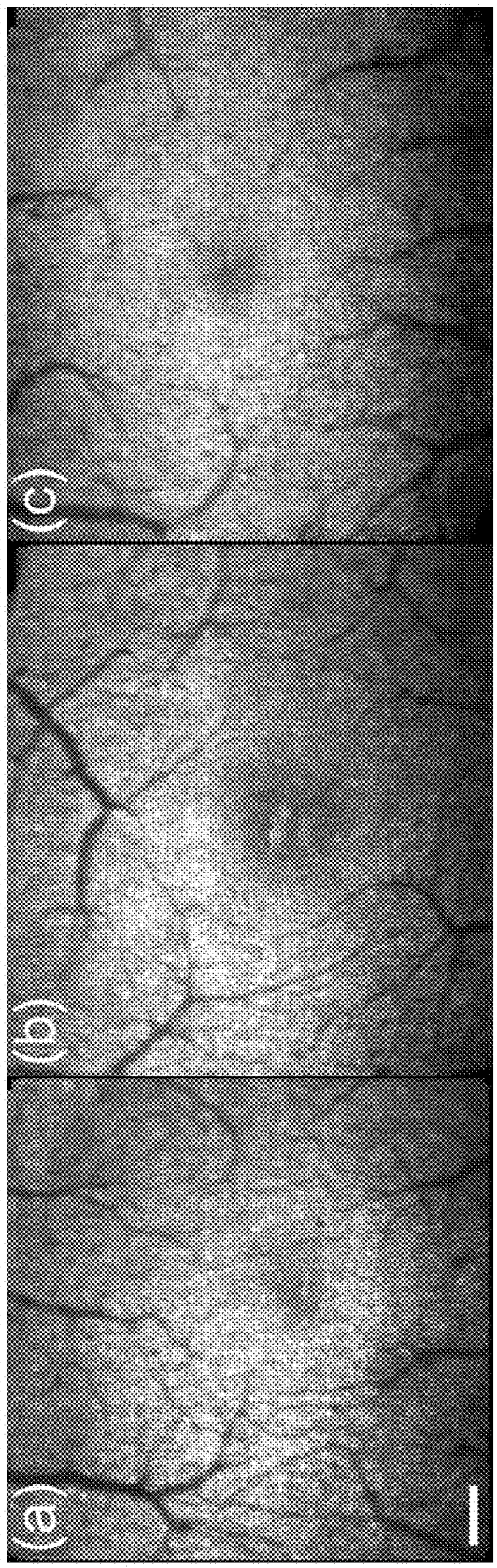
FIGS. 9A-C shows the ring of capillaries around the foveal avascular zones of three individuals.

FIGS. 9A-C shows the ring of capillaries around the foveal avascular zones of three individuals. These images are averaged from 50-70 individual registered video frames using the post-processing registration software described below. The scale bar is 200 μm.

Figure 10:
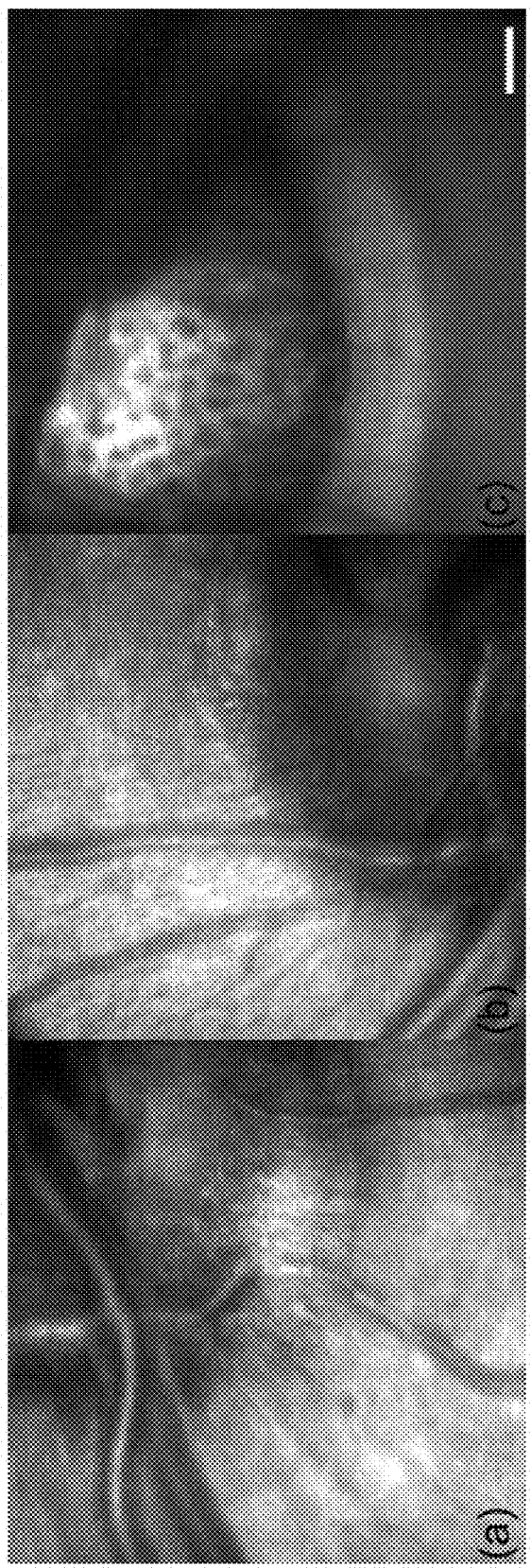
FIGS. 10A-C show three images of the optic nerve heads at different depths collected from three subjects.

On several subjects, the optic nerve head was also examined. FIGS. 10A-C show three images of the optic nerve heads at different depths collected from three subjects. FIG. 10A shows nerve fiber bundles and vessels at a shallow depth. Individual nerve fiber bundles entering the optic nerve head can be visualized when the system focus is set to more anterior (i.e., inner) layers. FIG. 10B shows photoreceptors visualized at the rim. Photoreceptors along the rim and in the scleral crescent can be seen as the focus is adjusted deeper. FIG. 10C shows the lamina cribrosa deep within the optic nerve head. When the focus is pushed deep into the optic nerve head, the vacuoles and sponge-like pattern of the lamina cribrosa can be seen.

Figure 11:
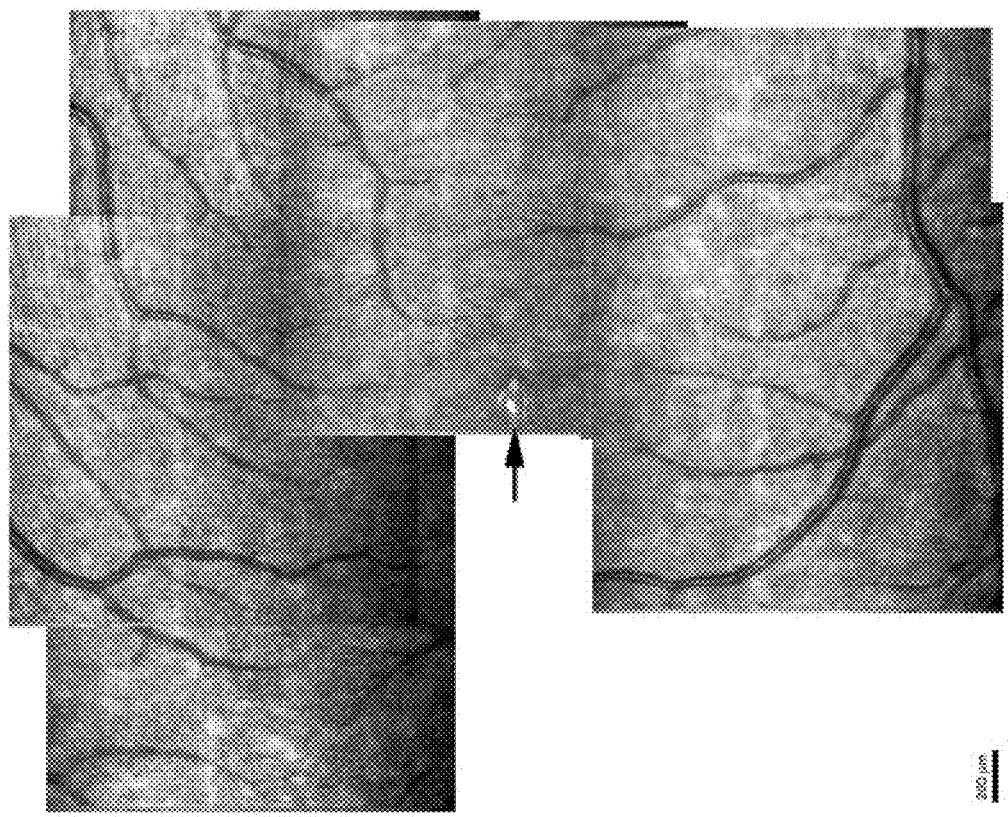
FIG. 11 depicts nerve fiber bundles in central macula.

FIG. 11 shows nerve fiber bundles in central macula. The arrow indicates location of fovea. In the youngest subject imaged (26 years old), individual bundles of the nerve fiber layer in the region immediately surrounding the fovea were visualized. The nerve bundles measured about 15-20 μm in diameter, consistent with known anatomical characteristics of the nerve fiber layer.

After a patient imaging session where videos are acquired, post-processing analysis can be conducted to transform the raw images into information that can be useful to the clinician to make diagnoses and/or guide therapies. Acquisition software and image collection protocol can be used, for example, for improved image registration and frame averaging, cone counting, and generation of macular montages. In some embodiments, the software is semi-automated and requires some user input.

Involuntary eye motion can be problematic for ophthalmic diagnostic techniques. The apparent motion with respect to the field size can increase as the field size decreases, and there should be no overlap between adjacent AOSLO images sized 1-2 deg. collected from a clinical population that includes poor fixators. Retinal tracking hardware can be integrated into AOSLOs, successfully stabilizing images to within about 15 μm. Real-time software registration algorithms have also been demonstrated, stabilizing images to less than a cone diameter when AO correction and patient fixation are good. Image registration and frame averaging can increase the signal-to-noise ratio, to increase the yield of useful frames with de-warping and to better resolve moving particles (e.g., blood cells flowing in capillaries) when long duration scans are required (e.g., autofluorescence of lipofuscin or other retinal fluorophores), and when a specific feature (e.g., photoreceptor, small capillary, etc.) needs to be tracked over time. The acquisition software can be used for both AOSLO and AO-LSO images, does not require perfect AO correction and can accept a lower than optimal yield (discarding non-overlapping and wholly distorted frames).

In general, eye motion can cause intra-frame distortions, compressing, expanding, or shearing pixels depending upon whether the movement is in the same, opposite, or orthogonal direction as the image scanner. Eye motion within a frame can also cause inter-frame translation between adjacent frames. Torsional eye motion can also cause one frame to rotate with respect to another. Eye motion is not fast enough to occur during the integration time of the linear detector (i.e., for the AO-LSO with line rates in the tens of kHz the integration time is usually less than about 100 μs), and which can be used as an advantage in the registration software. Processing can be done on strips 20 pixels in width, which can take about 1.3 ms to acquire (for a frame rate of 15 fps). The registration software can perform translation of these small image strips. In some embodiments, image de-warping (expansion, compression, or shear to compensate eye motion) is applied. If there are not matched features because of excessive warping, the region can be discarded. Image de-warping can be used to increase yield.

The registration software can align one frame to another (e.g., to correct for intra-frame eye motion), correct the distortions (e.g., expansion, compression, shear, rotation, etc.) within a frame (to correct for inter-frame eye motion), co-add images to reduce noise and increase signal-to-noise ratio, collect images in situations where the return from the eye is very dim (e.g., fluorescence), put together montages or mosaics (e.g., only the overlap regions are registered), extract eye movement data, align a second set of fluorescence images (e.g., dual registration technique), or any combination thereof.

In some embodiments, the registration software algorithm involves three steps. The first step can include choosing a key (or anchor) frame. This step can be performed manually, although the software can perform this step automatically using discrimination based upon image brightness, contrast, and/or frequency content. The second step can include executing a feature-matching routine to find similar structural features in the key frame and all others. The third step can include aligning all frames to the key frame.

In some embodiments, the first step includes making an initial pass on the images to select a key frame. The first step can be done by the operator of the system. Images with blinks or excessive eye motion can be removed in the initial step. In some embodiments, these frames can be automatically removed in subsequent steps because of a lack of matching features. The step of removing images with blinks or excessive eye motion can increase the processing speed by reducing the number of frames to process. The images to be processed can be smoothed with a median filter to remove some image noise and contrast stretched for image enhancement.

Figure 12:
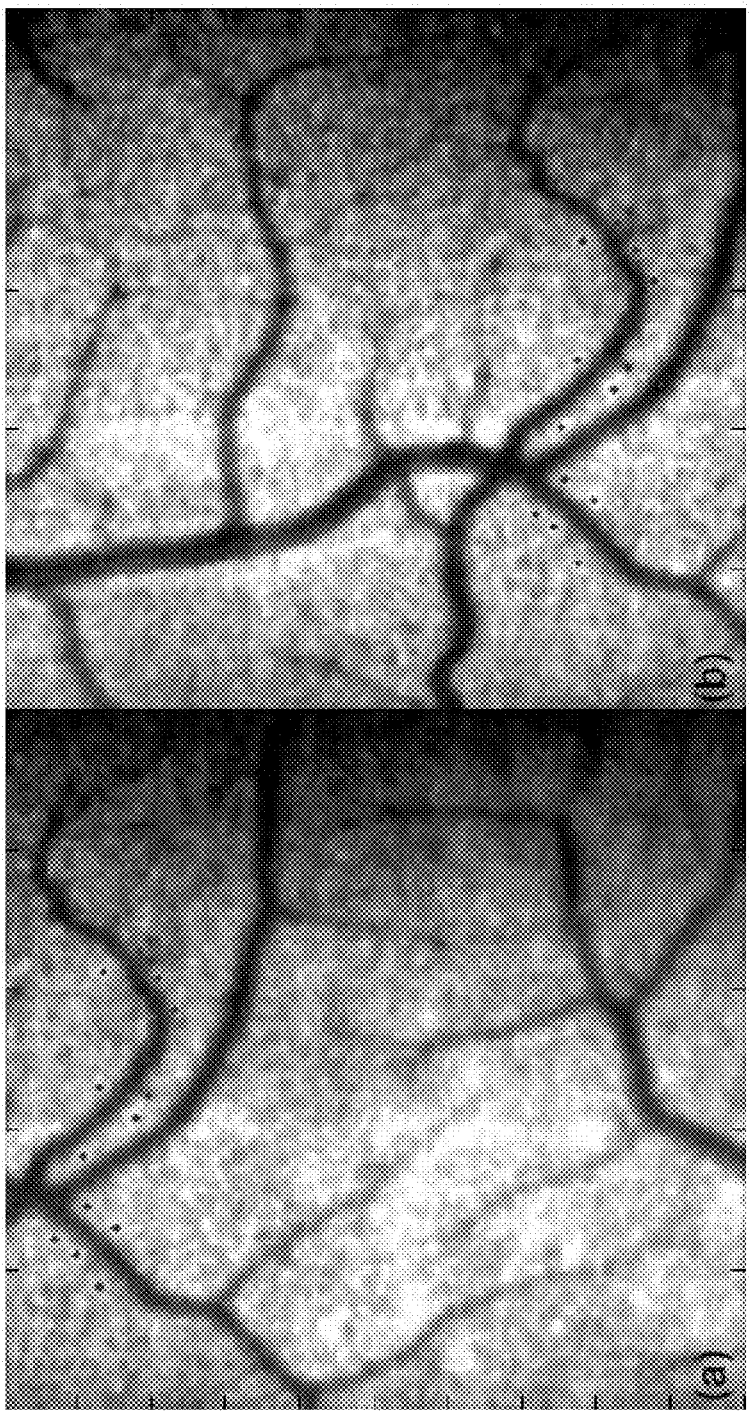
FIG. 12 shows two frames with matched features.

In some embodiments, the second step identifies structural features that are identical in the two frames (anchor frame and frame to be aligned). A feature matching algorithm, e.g., a scale invariant feature transform (SIFT), can be used. SIFT provides the coordinates and a descriptor (key) for each identified feature. The descriptor contains a series of parameters related to the geometrical characteristics of the feature and the intensity gradient around the feature, properties that are scale invariant in addition to rotation and translation invariant. Depending on the image content, there can be as many as 1000 SIFT features in a 500×500 pixel image. FIG. 12 shows two frames with features matched using SIFT.

Once the features are identified in a pair of images, the third step can be to match them. In some embodiments, the step of matching the images includes calculating the angle (e.g., the arccosine of the dot product between the two descriptors) between two descriptors. In some embodiments, the step of matching the images includes calculating the Euclidean distances. For small angles, the ratio of angles can be a close approximation, but more efficient to calculate, than the ratio of Euclidean distances. The matches where the ratio of vector angles from the nearest to second nearest neighbor is less than a pre-selected value (e.g., 0.6) can be kept. A larger value can generate more matching points but can add more false matches. There can be on the order of 100 matches for a pair of images. If there are less than ten matches, the result can be considered unreliable, the frame can be discarded from the set, and the next frame is considered.

Once the coordinates of all matched points in the anchor frame and frame to be aligned are found, a transformation between frames can be calculated. For simple whole frame translation, the average translation angle for all pairs of matched points can be found and converted into a single set of x-y displacement coordinates. Intra-frame motion can cause distortions where different parts of the image will translate by different distances and in different directions. The matched points can be filtered. A histogram (bin size=20 deg.) of the translation angles for all pairs of matched points can be calculated and analyzed. In some embodiments, if the histogram has only one maximum, this indicates simple translation and only the matched points from the bin corresponding to this maximum are kept. Translation angles outside of this bin can indicate false feature matching. If the histogram has two maxima, this can indicate that two parts of the frame move in different directions. The matched points from the bins corresponding to the two maxima can be kept and angles outside of these bins can be considered to be unreliable.

To perform a sophisticated transformation in the presence of complex eye motion, the frame to be aligned can be split into horizontal strips (e.g., 20-pixel thick horizontal strips). When a strip contains one or more matched points, it can be displaced by the average translation angle of the matched points within the strip. To find the transformation of strips without any matched points, x-y displacement coordinates can be calculated by interpolation of the displacement values of the first and the last valid strips (i.e., those with valid matched points). The final registered image can contain some discontinuities (i.e., black lines) if individual stripes are translated and full image de-warping is not performed.

To create a composite image of all frames without discontinuities, the non-zero image regions of the registered images can be averaged. The standard error can be calculated for each pixel in the non-zero image region. Standard error calculation can be used to obtain retinal capillary maps. The standard error can be expected to be larger over blood vessels due to the discrete motion of the blood cells and smaller where there are no blood vessels. Both the average image and each registered image can be filtered with a contrast enhancement filter.

FIGS. 13A-D show a comparison of registration techniques. FIG. 13A shows a single frame centered on the fovea of a subject. FIG. 13B shows a composite image of an 89-frame average using full frame registration technique. FIG. 13C shows an 89-frame average using the strip registration technique to correct translation and intra-frame distortion from eye motion. FIG. 13D shows an 89-frame average without registration. FIGS. 13B and 13C show improvement in vessel contrast (especially in the lower left portion of the image).

Acquisition software can include de-warping routines and software for automated registration (e.g., with automatic selection of anchor frames, etc.). In some embodiments, finding and matching SIFT points takes 8 seconds per frame on a standard laptop. The process can be improved for efficient computation and then implemented for real-time registration. The process can include correcting for second order torsional eye motion.

To robustly automate the cone counting procedure, several factors are controlled or accounted for, including but not limited to, inherent differences in photoreceptor reflectivity and size, variable brightness across the image field, poor AO correction, and eye motion induced distortions. Photoreceptor waveguiding can be caused by light interference between individual discs within the photoreceptors and can vary from cone to cone depending on its relative metabolic state. In addition, blood vessel shadows and other structures and layers (e.g., the never fiber layer) can induce changes in the reflectivity of the photoreceptor layer across the field. The AO-LSO can have a slight non-uniform illumination (e.g., from the cylindrical lens), and the field size is such, relative to the aplanatic patch, that AO correction can be more optimal in some regions than others.

Several cone counting algorithms are contemplated and can be implemented into the system. Besides selecting the region on which to perform cone counting, the software can be fully automated. Depending on the region size and cone density, the software can take a few seconds to several minutes to complete. The cone counting software can be used to quantify the photoreceptor density in a patch of the retina or to characterize density as a function of eccentricity (i.e., distance from the fovea). This can be used in studies of vision, myopia, many diseases, drug effectiveness, etc.

The algorithm for cone counting can first correct for a non-uniform image background. A 2×2 median filter can be first applied. The background can be obtained by morphologically opening the image using a disk-like structuring element with a radius of 5 pixels. After subtracting the background, contrast stretching can be performed for image enhancement. Regions with local maxima across the image can be identified, and an initial estimate of each cone location can be determined from the centroid of the local region. Finally, the cone locations can be filtered to prevent duplicate locations from closely-spaced centroids.

Filtering can be accomplished by obtaining a rough estimate for the cone diameter by morphologic transformation, thresholding, and statistical analysis to determine the average cone area across the entire region. A region about 1.4 times the average cone diameter around each centroid (cone) can be examined to determine if multiple centroids exist within the region, indicating potential overlapping cones. If multiple centroids exist, filtering can include calculating the mean intensity within the expanded region for each centroid and keeping the cone with the maximum mean intensity. The 1.4 factor can be adaptively corrected using frequency analysis for different cone densities (e.g., found at different eccentricities).

FIGS. 14A-C show a comparison between manual and automated cone counting at an eccentricity of 0.8 mm. A region sized 50×50 pixel was chosen. When regions sized 100×100 pixels were chosen so as not to overlap with retinal vessels, the automated software produced similar cone counts as the 50×50 pixel regions.

FIG. 14A shows a full frame showing location of 50×50 pixel regions selected for cone counting. FIG. 14B shows a filtered 50×50 pixel region used in the automated software. Cone locations are shown with solid red circles in the overlay. FIG. 14C shows an unfiltered 50×50 pixel region used for manual counting. Cone locations are shown with solid circles (automated counts) and open circles (manual counts) in the overlay. The cone counts for the 50×50 pixel region were 140 for the manual counts and 121 for the automated counts (about a 13% difference). The locations of the counted cones can overlap for manual and automated analysis for a large fraction of cones. Even when the locations do not overlap because of pixel-to-pixel intensity variation and the manner in which the automated software chooses the centroid, the automatic software algorithm still counted a cone with nearly 90% accuracy. For the AO-LSO at eccentricities less than about 0.8 mm, the 2×2 median filter begins to influence the cone counts because cone peaks and contrast can be smoothed out by the median filter. Conversely, removing the median filter can cause the counts for large eccentricities to become artificially inflated.

Montages can be formed manually or automatically. The montages shown above in FIGS. 6 and 11 were stitched manually. Stitching software for automatic montages can perform two basic tasks. First, the software determines the location of the individual frames within the montage (using correlation in the overlapping regions). The software can do this from the unpacked and unprocessed video files acquired at each location. Second, the software can blend the frames so there is no discontinuity at the boundaries of the individual frames.

Initially, one video frame at each retinal location can be selected, which can be automated. The SIFT keys can be determined for each image as described in the registration and frame averaging section. The key matching can be performed for different frame pair combinations. Frame pairs without any overlapping region will have no matching points. The frame that has the most connections to other frames can be selected as anchor. The stripes within all the frames connected to the anchor can be aligned given the displacement with respect to the anchor calculated for each frame. Since the alignment can occur using thin stripes in a similar manner as the averaging previously described, intraframe motion that may corrupt the alignment between two non-anchor frames should be reduced. The software can search for frames linked to this first set of frames and stitch them to the mosaic. The search continues until all the linked frames are stitched to the mosaic. For seamless patching, multi-band blending can be used.

Figure 15A:
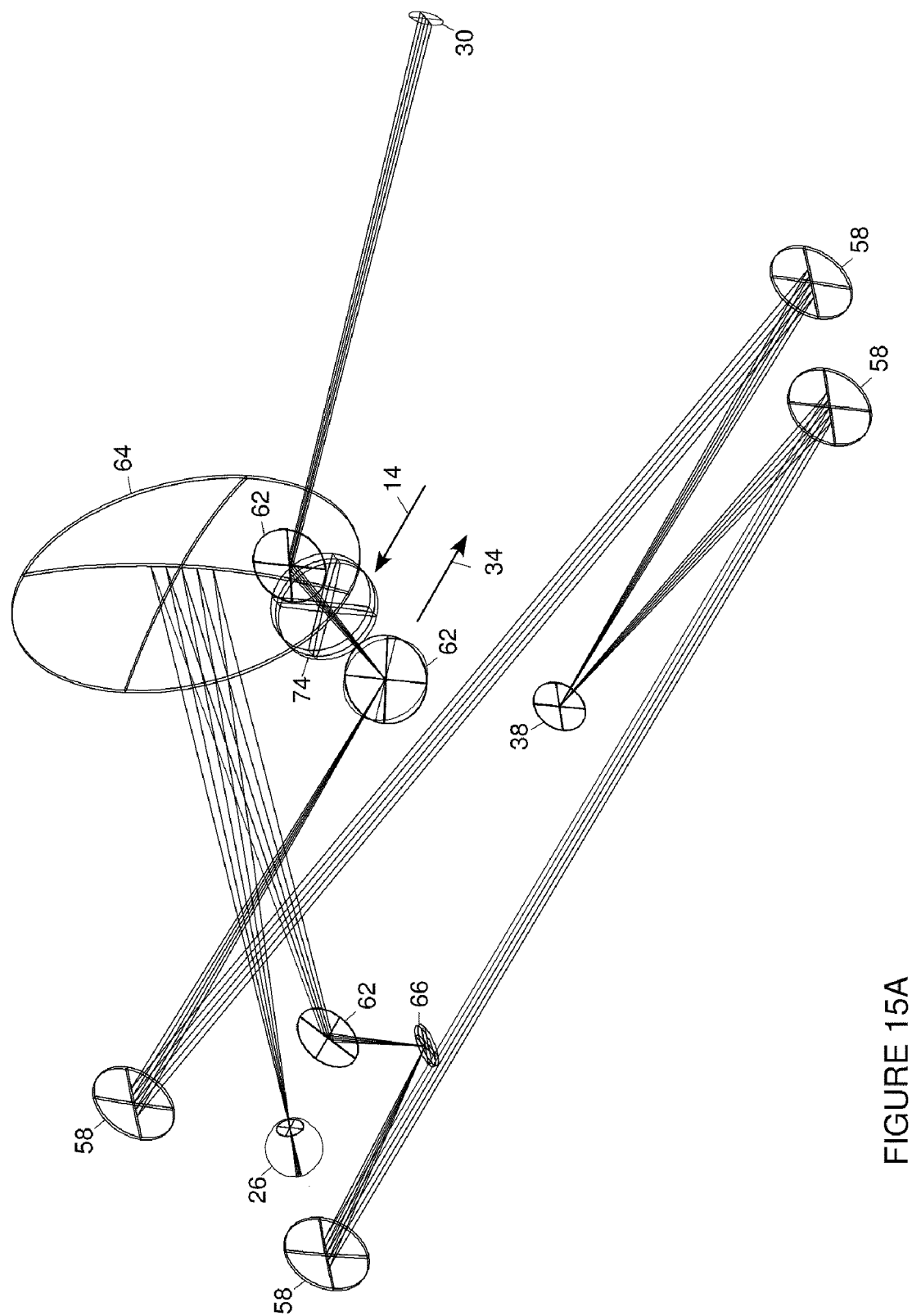
FIG. 15A shows a schematic diagram for the optical layout of another AO-LSO.

An optical arrangement that can fit on a plate of, for example, 12×18 inches (30×45 cm) can be used for rapid automated montaging. The AO-LSO system can be mounted on a modified slit lamp stand (or similar configuration) so that the instrument can be positioned in front of the patient (rather than visa versa). FIG. 15A shows a schematic diagram for the optical layout of an AO-LSO, and FIG. 15B shows an AO-LSO through-focus spot diagram.

The fifth spherical mirror 64 can be about double in size (from 2 inches to 4 inches) to accommodate field offset correction for automatic montaging. The field can be shifted along the scan by applying voltage offsets to the saw-tooth ramp that drives the galvanometer. The scanner 66 can be mounted to a small stepper motor (or galvanometer) so that offsets can be applied to the field in the opposite axis. The overall clinical performance advantage gained with automatic montaging can outweigh the small amount of additional system complexity. In the clinic, once the subject is aligned, 3×3 montages that cover the entire macula (12-15 deg.) or another target, where each position is comprised of 25 frames, can be acquired in as little as 20 seconds (with a conservative 1 second settling time between positions). Configuration for rapid and automatic montaging can also reduce the amount of eye motion that the post-processing software has to contend with. Automatic montaging can be used in the AO-LSO system for "smart" scanning with unique hardware configurations and fully automated software control.

Figure 15B:
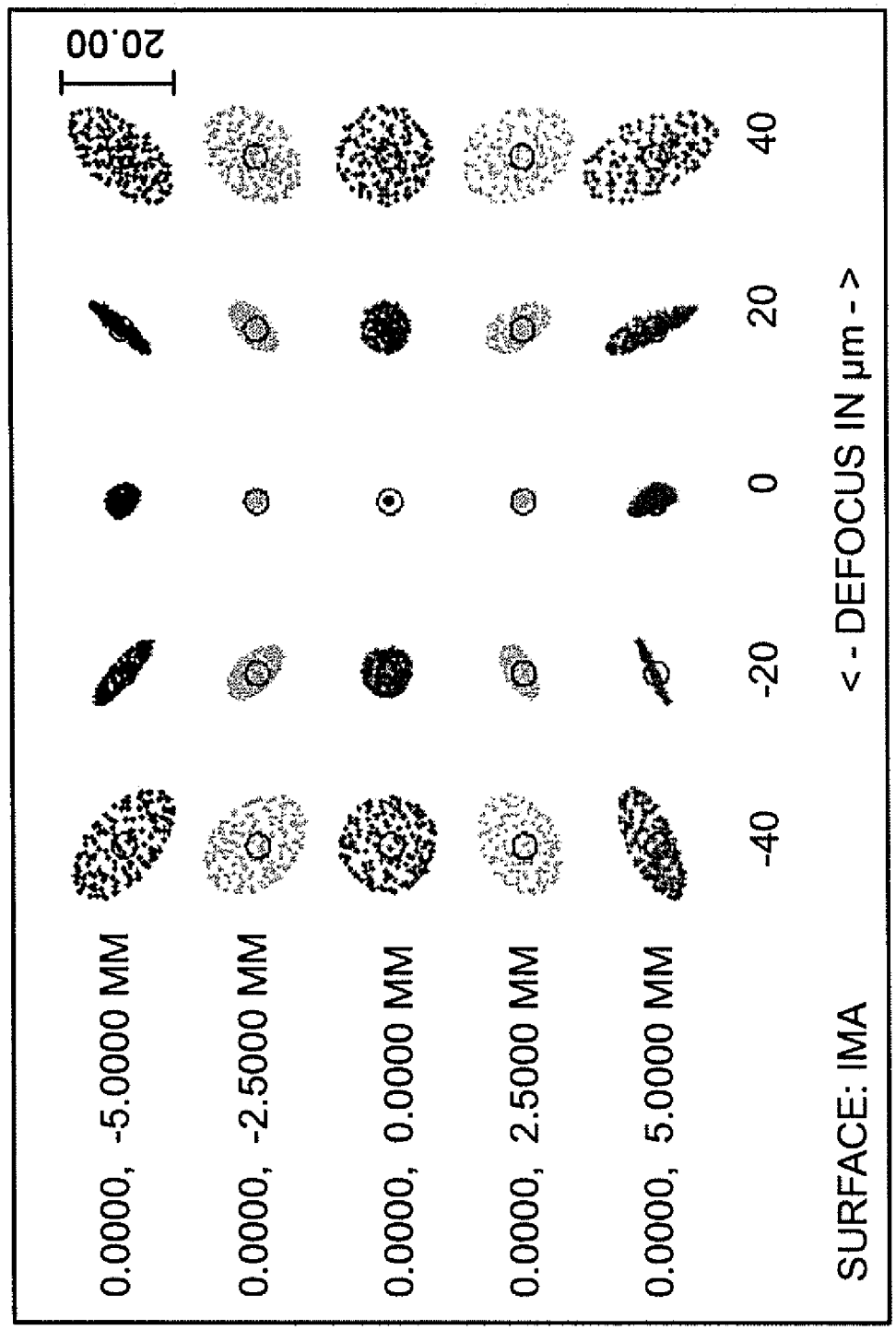
FIG. 15B shows an AO-LSO through-focus spot diagram.

The spot diagram shown in FIG. 15B is similar to the spot diagram shown in FIG. 3B. There is some slight degradation in optical performance that is a consequence of the tighter, shorter optical paths (i.e., the radii of curvature and hence focal lengths of all five spherical mirrors were decreased by about 33% to produce the smaller instrument footprint). The predominant aberration is first-order astigmatism and the magnitude of the system aberrations can be corrected by the large-stroke deformable mirror.

The aplanaticity of the optical system (the degree of compensation for spherical aberration and off-axis coma) was characterized in ZEMAX. The aplanatic region or "patch" was effectively set as part of the system design (with AO minor corrections through the third order) so that the total residual aberrations beyond these low orders across the 5.5 deg field did not exceed the Airy disc diameter at the perimeter, and so that the required low-order AO corrections (other than sphere) did not exceed the stroke of the mirror in any part of the field of regard of the large final mirror. Furthermore, there is no single astigmatism correction (the dominant aberration of off-axis spherical minors) that can compensate fully across large field angles. These aberrations can have the effect of limiting how short the focal lengths can be in the optical train relative to the field size, independent of the real eye, that represent an irreducible "pseudo-aplanatic" patch size of the optical system over which high quality diffraction-limited focus is maintained. The eye itself with larger pupils (though already reasonably aplanatic) can contribute irreducible aberrations and further reduce the effective size of the aplanatic region.

In practice, a more severe limitation on the effective aplanaticity of the focal region can arise from the gross tilt of the focal plane with respect to the retina across the field. This can be the case in myopes where the lengthened eye can tilt the retina away from the ideal emmetropic posterior pole surface or with eccentric pupil alignment. The AO-LSO can address this in some circumstances (nasal-temporal tilt) by tilting the detector surface (with a rotary mount) in the plane of the line focus to compensate—the equivalent of moving a point detector axially at the line rate to adjust focus on the fly—which cannot be done with an SLO imaging system. The vertical extent of the scan can be reduced to limit the (superior-inferior tilt) error of the mosaic patch, and can be compensated for with more patches.

The AO-LSO can include an illumination source having an output power exceeding about 10 mW out of the fiber. The line scanning approach is inherently safer than a flying spot because it only focuses onto the retina in one dimension, and the AO-LSO is eye safe up to several tens of mW at our field size (5.5 deg.). Preliminary calculations using an 830-nm center wavelength and an exposure duration of 100 sec. results in a MPE threshold of 32.6 mW. A 2-mW illumination beam at the cornea is roughly 16 times below the safety threshold. Even for the most conservative exposure duration (30,000 sec., or an 8 hour day), the MPE is 10.3 mW, and a 2-mW beam is 5 times below the safety threshold.

In some embodiments, the linear detector has 1024 pixels and line rates up to 53 kHz. The linear detector can have line rates up to about 15.4 kHz (15 fps) to achieve the imaging signal-to-noise ratio require for to produce high quality images in subjects without dilation. The linear array detector (e.g., Sprint, Basler Vision Inc.) can have 2048 pixels and a line rate of 70 kHz. The linear array detector can have pixels in the range of about 5 µm to about 6 µm.

Higher power imaging sources and higher quality detectors can allow for higher acquisition speeds with concomitant shorter imaging sessions, better image SNR, and the potential for exploration of functional retinal characteristics such as hemodynamics. With AO, individual leukocytes can be tracked in the capillaries around the foveal avascular zone and in areas of wet age-related macular degeneration and diabetic retinopathy.

With the use of a wavefront sensorless algorithm, the system does not require separate hardware to sense the optical aberrations. The wavefront sensorless algorithm can use image information to provide a measure of the ocular aberrations that can then be passed to the wavefront compensator to provide AO correction. Information extracted from the image sensor can be used to calculate the sample aberrations that are applied to the correcting element, obviating the need for a separate wavefront sensor. The wavefront sensorless algorithm can operate by three steps. First, aberration information (an optimization metric) can be extracted from the image sensor. This can sometimes be accomplished from a single image or set of images with phase retrieval and diversity methods; however, in some cases, these do not converge to a unique solution for an arbitrary object. An intensity or image metric can be measured while the adaptive element is configured with a sequence of known trial aberrations. The second step in the algorithm can be to calculate a correction, and this can be done by expansion into orthogonal components (modal aberration expansion). The third step can be to apply the estimated correction iteratively until the image quality is optimized. The optimization algorithm and parameters used, as well as the magnitude of aberrations and object characteristics, can determine the speed to which solution converges and final resultant image quality.

"Model-free" optimization algorithms (e.g., such as hill climbing, conjugate gradient descent, etc.) use stochastic and adaptive search methods with empirically-determined parameters. Separation of the inherent image information from the aberrations can be difficult for these algorithms. Other "model-based" optimization algorithms use knowledge of the optimization function to achieve more efficient convergence. These deterministic, non-adaptive algorithms work by choosing the appropriate trial aberration to apply to the deformable mirror or other corrective element, but also in selection of the parameters for the search algorithm to achieve more rapid convergence.

The pinhole and single point detector of an SLO can limit the magnitude of aberrations that can be sensed with a wavefront sensorless method. Large aberrations can direct the light out of the pinhole. Other techniques achieved large aberration correction using a CCD camera with spatially-weighted sensitivity, a rms spot radius optimization metric, and a Lukosz-Zernike (LZ) aberration representation more suitable to that metric. This algorithm can specify a minimum of N+1 photodetector measurements to correct N aberration modes. Other model-based image optimization algorithms required 3N images for each mode. Correcting up to 5 orders of Zernike polynomial modes can include at least 20 photodetector measurements and 60 images. The AO closed loop bandwidth can be proportional to the image frame rate and the deformable mirror temporal response (i.e., the speed with which the deformable minor is able to sequence through the trial aberration modes).

Figure 16:
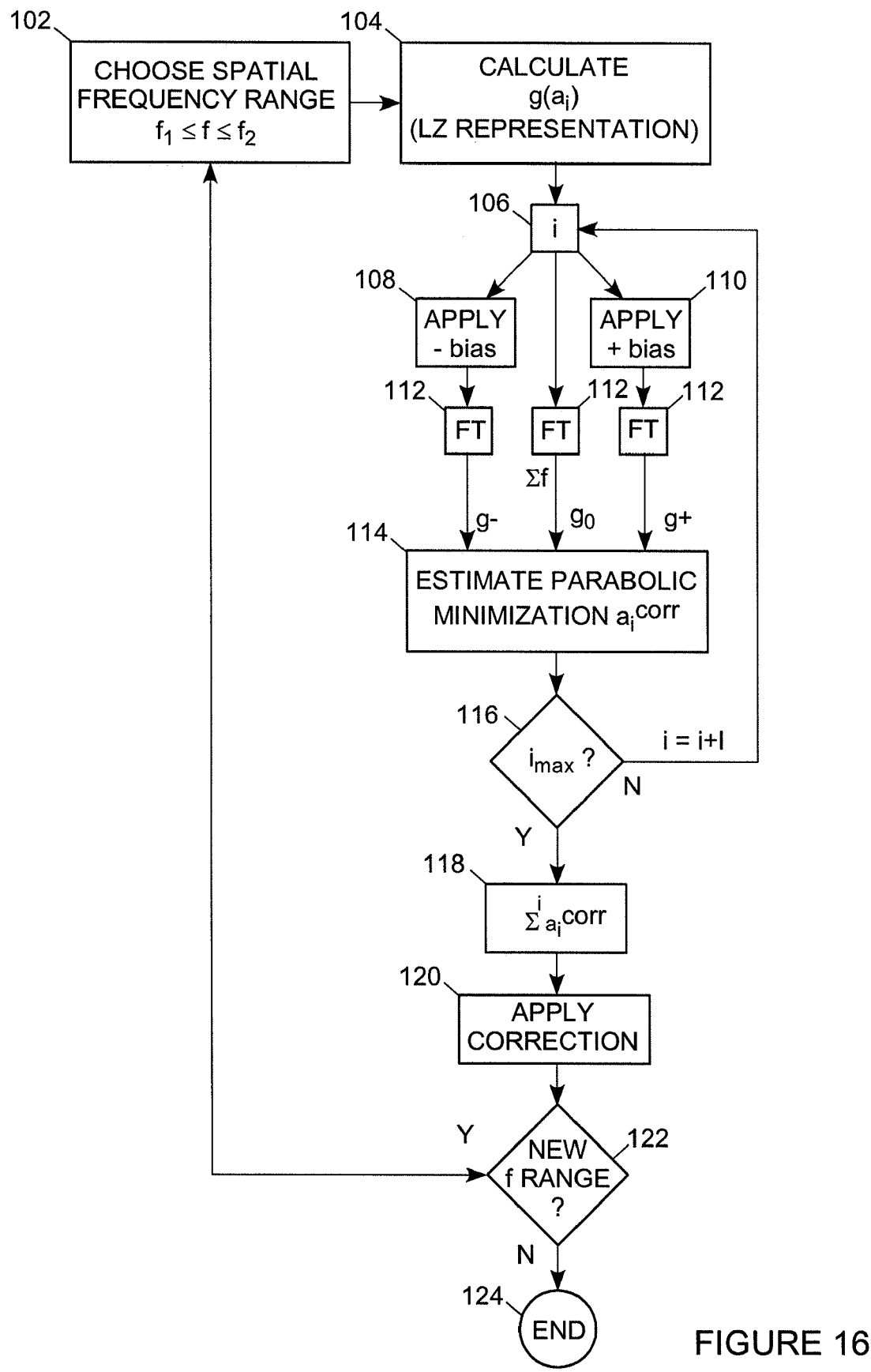
FIG. 16 depicts a flow diagram of a wavefront sensorless algorithm.

FIG. 16 shows a flow diagram of a wavefront sensorless algorithm. An image quality metric based upon low frequency content is utilized, using an optimization metric ($g(a_i)$, where $a_i$ are the aberrations coefficients) specifically derived for the one-dimensional case of the AO-LSO. N is the frequency of the linear detector (~15 kHz) and so a correction rate of ~375 Hz can be obtained for 5 aberration mode orders. The model-based optimization metric is independent of the object structure, uses low frequencies content but is capable of correcting all spatial frequencies, has a paraboloidal shape suited to simple maximization algorithms, allows independent maximization for each LZ coefficient, and also permits ranging of the spatial frequencies for correction of larger magnitude aberrations.

Once the derived optimization metric is calculated for a specific set of aberrations coefficients and a specific frequency range (depending upon aberration magnitude), the aberration correction process (metric maximization) is run. This involves making an unbiased measurement once and positive and negative bias measurements for each aberration mode from the linear fast Fourier transform. The optimal correction is calculated by parabolic minimization of the reciprocal of the measured aberration function for that mode. Once all modes have been estimated, they are summed and the resultant correction applied to the deformable mirror. If multiple magnitude ranges are required, the process can be repeated for other frequency ranges.

The AO controller and LSO image acquisition software can be merged into a single user interface. In some embodiments, an automated analysis software platform is used in the AO-LSO system to conduct image registration, photoreceptor counting, and stitching, as well as imaging processing and enhancement (e.g., image and video saving and compression, scaling, alternate color maps, contrast stretching, histogram equalization, etc.). The software can include automated selection of anchor frame, motion de-warping for increased yield, correction of higher order movements such as torsional eye motion, and efficiency enhancement for real-time operation. The software can be automated to operate cone counting on large region sizes.

The acquisition software can include a uniform interface to the database so that scan parameters and protocol information can be extracted when required during a particular analysis type. For example, the scan sequence offsets can be managed so that during stitching, the individual frames can automatically positioned in the correct order prior to cross correlation and blending. These types of operations can occur automatically without user input so that the clinician can focus on disease detection, diagnosis, and treatment, rather than on software operation issues.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., a digital signal processor (DSP), an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The terms "module" and "function," as used herein, mean, but are not limited to, a software or hardware component which performs certain tasks. A module may advantageously be configured to reside on addressable storage medium and configured to execute on one or more processors. A module may be fully or partially implemented with a general purpose integrated circuit (IC), DSP, FPGA or ASIC. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. Additionally, the components and modules may advantageously be implemented on many different platforms, including computers, computer servers, data communications infrastructure equipment such as application-enabled switches or routers, or telecommunications infrastructure equipment, such as public or private telephone switches or private branch exchanges (PBX). In any of these cases, implementation may be achieved either by writing applications that are native to the chosen platform, or by interfacing the platform to one or more external application engines.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks. Communication networks can also all or a portion of the PSTN, for example, a portion owned by a specific carrier.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific illustrative embodiments, it should be understood that various changes in form and detail may be made without departing from the spirit and scope of the invention.

What is claimed is:

1. An apparatus comprising:
    a source of optical radiation;
    a line generator configured to receive the optical radiation and to form the optical radiation into a line of light;
    a first optical module configured to (i) scan a portion of an eye with the line of light, (ii) descan reflected light from the scanned portion of the eye and (iii) confocally provide output light in a line focus configuration;
    a detection device configured to detect the output light and to image the portion of the eye; and
    a second optical module configured to (i) detect an optical distortion and (ii) correct the optical distortion in the line of light scanned on the portion of the eye.

2. The apparatus of claim 1 wherein the detection device is a linear array detector.

3. The apparatus of claim 1 wherein the second optical module detects the optical distortion in an image from the detection device.

4. The apparatus of claim 1 wherein the second optical module comprises:
    a wavefront sensor adapted to detect the optical distortion; and
    a wavefront compensator adapted to correct the optical distortion in the line of light scanned on the portion of the eye.

5. The apparatus of claim 1 wherein the second optical module comprises a deformable minor adapted to correct the optical distortion in the line of light scanned on the portion of the eye.

6. The apparatus of claim 5 further comprising at least one optical relay configured to direct the line of light to the deformable mirror.

7. The apparatus of claim 1 wherein the second optical module comprises a second light source and a second optical element adapted to allow a portion of the light from the second source to pass to a wavefront sensor.

8. The apparatus of claim 7 wherein the second optical element includes a pellicle beamsplitter, dichroic beamsplitter, or any combination thereof.

9. The apparatus of claim 1 further comprising a processor in communication with the detection device and the second optical module, the processor configured to determine the optical distortion based on at least one image from the line of light.

10. The apparatus of claim 1 further comprising a processor in communication with the detection device and the second optical module, the processor configured to register an image from the line of light, count cones in an image from the line of light, or any combination thereof.

11. The apparatus of claim 10 wherein the processor is configured to:
    choose a key frame in the image from the line of light;
    identify similar structural features in the key frame and at least one other frame in the image from the line of light; and
    align the at least one other frame to the key frame to register an image from the line of light.

12. The apparatus of claim 10 wherein the processor is configured to:
    correct for a non-uniform image background in the image from the line of light;
    subtract the background and enhance the image from the line of light; and
    identify regions with local maxima to obtain an estimate of each cone location based on a centroid of the region.

13. A method for imaging a portion of an eye, comprising:
    forming optical radiation into a line of light;
    scanning a portion of the eye with the line of light;
    descanning reflected light from the scanned portion of the eye;
    confocally providing output light in a line focus configuration to a detector;
    imaging, with the detector, the portion of the eye from the output light;
    detecting an optical distortion; and
    correcting the optical distortion in the line of light scanned on the portion of the eye.

14. The method of claim 13 further comprising detecting the optical distortion from an image from the detector.

15. The method of claim 13 further comprising detecting, by a wavefront sensor, the optical distortion and correcting, with a wavefront compensator, the optical distortion.

16. The method of claim 13 further comprising correcting, by a deformable mirror, the optical distortion in the line of light scanned on the portion of the eye.

17. The method of claim 13 further comprising using light from a second light source to detect the optical distortion.

18. The method of claim 13 further comprising registering an image from the line of light by:
    choosing, by a computing device, a key frame in the image from the line of light;
    identifying, by the computing device, similar structural features in the key frame and at least one other frame in the image from the line of light; and
    aligning, by the computing device, the at least one other frame to the key frame to register an image from the line of light.

19. The method of claim 13 further comprising counting cones in an image of the eye by:
    correcting for, by a computing device, a non-uniform image background in the image from the line of light;
    subtracting, by the computing device, the background and enhance the image from the line of light; and
    identifying, by the computing device, regions with local maxima to obtain an estimate of each cone location based on a centroid of the region.

20. A method for imaging a portion of an eye, comprising:
    forming optical radiation into a line of light;
    imaging a portion of an eye with the line of light;
    detecting an optical distortion in an image of the portion of the eye; and
    correcting the optical distortion in the light of light that images the portion of the eye.

21. The method of claim 20 further comprising imaging the portion of the eye to a wavefront sensor to detect the optical distortion.

22. The method of claim 20 further comprising processing at least one image from the line of light to detect the optical distortion.

23. The method of claim 20 further comprising compensating for the optical distortion with an adaptive optical element.

24. An apparatus comprising:
- a source of optical radiation;
- a cylindrical lens configured to receive the optical radiation and to form the optical radiation into a line of light;
- an optical system including a scanner and at least one focusing element, the scanner configured to scan a portion of an eye with the line of light and to descan reflected light from the portion of the eye, the scanner and the at least one focusing element configured to confocally provide output light in a line focus configuration;
- a linear array detector configured to detect the output light in the line focus configuration and to image the portion of the eye;
- a wavefront sensor adapted to detect an optical distortion; and
- a wavefront compensator adapted to correct the optical distortion in the line of light scanned on the portion of the eye.

* * * * *